US011548916B2

(12) United States Patent
Krismer et al.

(10) Patent No.: US 11,548,916 B2
(45) Date of Patent: Jan. 10, 2023

(54) ANTI-INFECTIVE COMPOUND

(71) Applicant: Eberhard Karls Universitaet Tuebingen, Tuebingen (DE)

(72) Inventors: Bernhard Krismer, Kirchentellinsfurt (DE); Andreas Peschel, Leinfelden-Echterdingen (DE); Stephanie Grond, Tuebingen-Hirschau (DE); Alexander Zipperer, Tuebingen (DE); Martin Christoph Konnerth, Tuebingen (DE); Daniela Janek, Tuebingen (DE); Hubert Kalbacher, Tuebingen (DE); Nadine Anna Schilling, Tuebingen (DE)

(73) Assignee: Eberhard Karls Universitaet Tuebingen, Tuebingen (DE)

( * ) Notice: Subject to any disclaimer, the term of this patent is extended or adjusted under 35 U.S.C. 154(b) by 0 days.

(21) Appl. No.: 16/986,926

(22) Filed: Aug. 6, 2020

(65) Prior Publication Data
US 2021/0024580 A1 Jan. 28, 2021

Related U.S. Application Data

(60) Division of application No. 15/713,103, filed on Sep. 22, 2017, now Pat. No. 10,774,113, which is a continuation-in-part of application No. PCT/EP2016/056358, filed on Mar. 23, 2016.

(30) Foreign Application Priority Data

Mar. 23, 2015 (EP) .................................. 15160285

(51) Int. Cl.
| | |
|---|---|
| *A61K 35/741* | (2015.01) |
| *A61K 38/12* | (2006.01) |
| *C07K 7/56* | (2006.01) |
| *C07K 11/02* | (2006.01) |
| *A61K 38/15* | (2006.01) |
| *A61P 31/04* | (2006.01) |
| *C12P 21/02* | (2006.01) |
| *A61K 38/00* | (2006.01) |

(52) U.S. Cl.
CPC .............. *C07K 7/56* (2013.01); *A61K 35/741* (2013.01); *A61K 38/12* (2013.01); *A61K 38/15* (2013.01); *A61P 31/04* (2018.01); *C07K 11/02* (2013.01); *C12P 21/02* (2013.01); *A61K 38/00* (2013.01)

(58) Field of Classification Search
CPC .............. A61K 38/15; A61K 2035/11; A61K 2035/115; A61K 66/74; A61K 66/741; A61K 38/12; A61K 35/74; A61K 35/741; C07K 11/02; C07K 7/56
See application file for complete search history.

(56) References Cited

U.S. PATENT DOCUMENTS

| | | | |
|---|---|---|---|
| 8,809,494 | B2 | 8/2014 | Bergman et al. |
| 9,458,200 | B2 | 10/2016 | Kalesse et al. |
| 10,774,113 | B2 * | 9/2020 | Krismer ................. C07K 7/56 |
| 2005/0244914 | A1 | 11/2005 | Liu et al. |
| 2009/0239216 | A1 | 9/2009 | Sasatsu et al. |
| 2014/0357563 | A1 | 12/2014 | Poncz et al. |

FOREIGN PATENT DOCUMENTS

| | | |
|---|---|---|
| CN | 101845081 A | 9/2010 |
| DE | 102005055944 A1 | 7/2007 |
| EP | 0932613 A1 | 8/1999 |
| JP | 2011-525512 A | 9/2011 |
| WO | WO-2006/073133 A1 | 7/2006 |
| WO | WO-2019046801 A * | 3/2019 ........... A61K 9/0014 |

OTHER PUBLICATIONS

Carnio et al., Pyridinyl polythiazole class peptide antibiotic micrococcin P1, secreted by foodborne *Staphylococcus equorum* WS2733, is biosynthesized nonribosomally, Eur. J. Biochem., 268(24):6390-401 (2001).
Donia et al., Mollamides B and C, Cyclic hexapeptides from the indonesian tunicate Didemnum molle, J. Nat. Prod., 71(6):941-5 (2008).
Ferrari et al., Antibiotics A21459 A and B, new inhibitors of bacterial protein synthesis. II. Structure elucidation, J. Antibiot. (Tokyo), 49(2):150-4 (1996).
Heilbronner et al., Genome sequence of *Staphylococcus lugdunensis* N920143 allows identification of putative colonization and virulence factors, FEMS Microbiol. Lett., 322(1):60-7 (2011).
Igarashi et al., Pargamicin A, a novel cyclic peptide antibiotic from *Amycolatopsis* sp, J. Antibiot. (Tokyo), 61(6):387-93 (2008).
International Search Report and Written Opinion, International Application No. PCT/EP2016/056358, dated Jun. 8, 2016.
Jones, "Amino Acids and Peptides", Royal Society of Chemistry, vol. 23, pp. 166-170 (Jan. 1, 1992).
Krismer et al., "Nutrient Limitation Governs *Staphylococcus aureus* Metabolism and Niche Adaptation in the Human Nose," PLOS Pathogen 10(1):e1003862 (2014).
Krismer et al., Nutrient limitation governs *Staphylococcus aureus* metabolism and niche adaptation in the human nose, PLoS Pathog., 10(1):e1003862 (2014).
Martin et al., Kocurin, the true structure of PM181104, an antimethicillin-resistant *Staphylococcus aureus* (MRSA) thiazolyl peptide from the marine-derived bacterium Kocuria palustris, Mar. Drugs, 11(2):987-98 (2013).

(Continued)

*Primary Examiner* — Jeffrey E. Russel

(74) *Attorney, Agent, or Firm* — Marshall, Gerstein & Borun LLP

(57) ABSTRACT

The invention relates to novel infective agents, the use thereof for the production of a pharmaceutical composition for the treatment and prophylaxes of a disease, preferably an infectious disease, a pharmaceutical composition comprising said compound, and to methods of producing said compounds. The invention further relates to a new probiotic configured for preventing or reducing the colonization by a pathogenic microorganism of an organ of a living being.

12 Claims, 11 Drawing Sheets
Specification includes a Sequence Listing.

(56) References Cited

OTHER PUBLICATIONS

Tabata et al., Zelkovamycin, a new cyclic peptide antibiotic from *Streptomyces* sp. K96-0670. II. Structure elucidation, J. Antibiot., 52(1):34-9 (1999).

Wanke et al., *Staphylococcus aureus* skin colonization is promoted by barrier disruption and leads to local inflammation, Exp. Dermatol., 22(2):153-5 (2013).

Wyatt et al., *Staphylococcus aureus* nonribosomal peptide secondary metabolites regulate virulence, Science, 329(5989):294-6 (2010).

Zipperer et al., "Human commensals producing a novel antibiotic impair pathogen colonization," Nature 535:511-516 (2016).

\* cited by examiner

☒ S.aureus ☐ S.lugdunensis WT

☒ S.aureus ☐ S.lugdunensis Δnrps4

☒ S.aureus ☐ S.lugdunensis Δnrps4

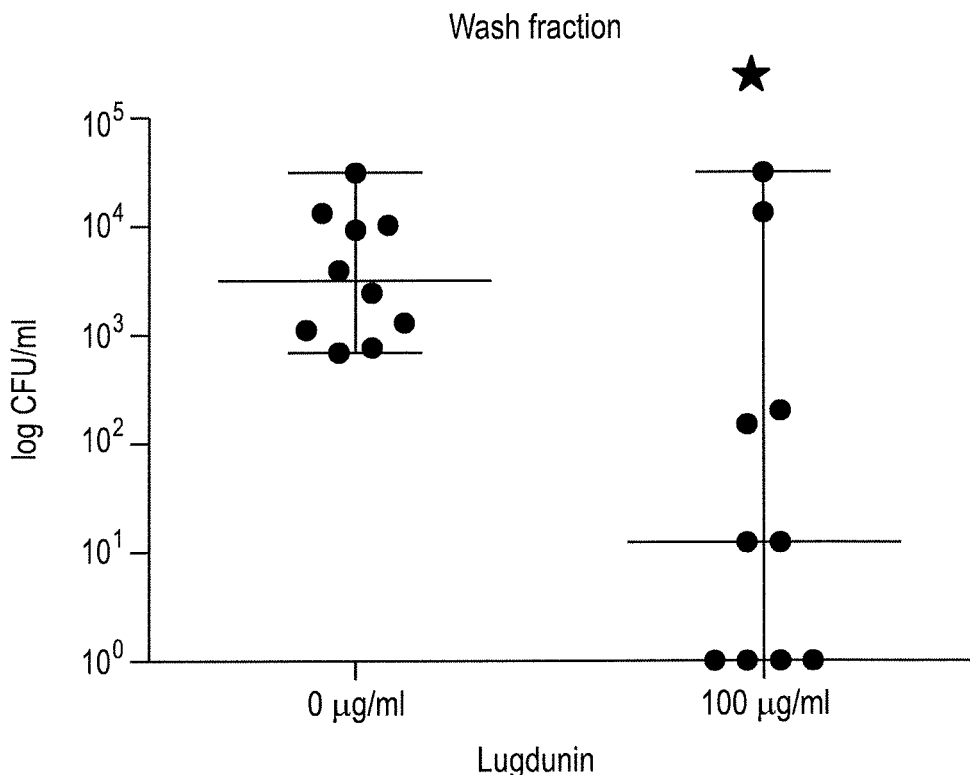
Fig. 8
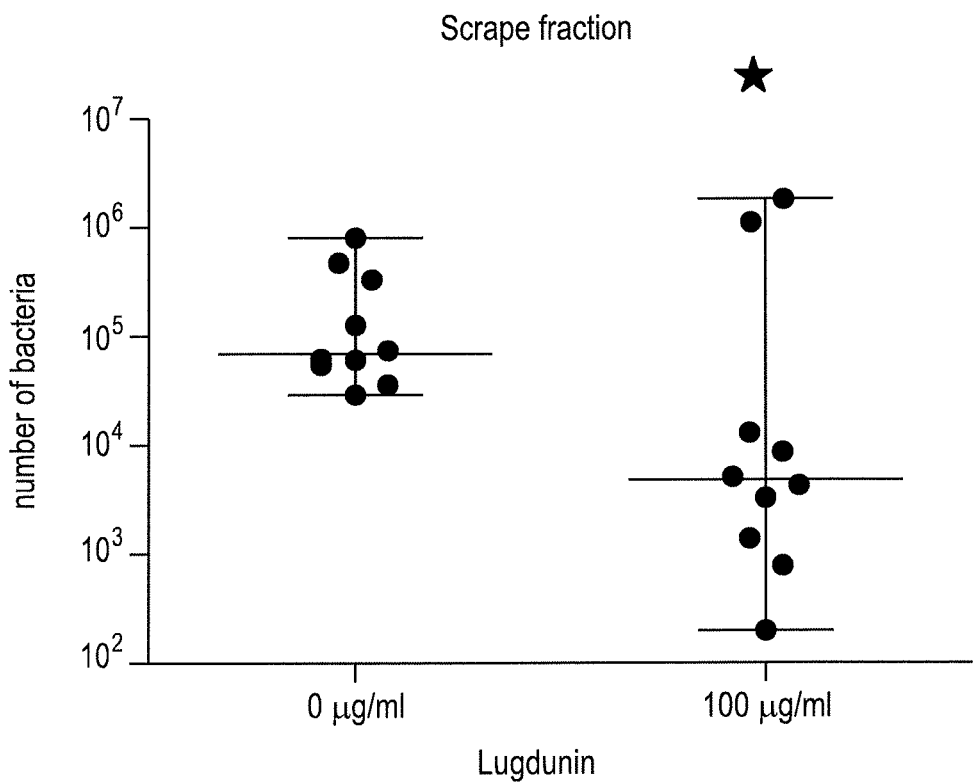

ANTI-INFECTIVE COMPOUND

CROSS-REFERENCE TO RELATED APPLICATIONS

This application is a divisional of U.S. application Ser. No. 15/713,103 filed 19 May 2020, which is a continuation in part of co-pending international patent application PCT/EP2016/056358 filed on 23 Mar. 2016 and designating the U.S., which has been published in English, and claims priority to European patent application EP 15 160 285.1 filed on 23 Mar. 2015. The entire contents of these prior applications are incorporated herein by reference.

REFERENCE TO A SEQUENCE LISTING

This application contains reference to amino acid sequences and/or nucleic acid sequences which have been submitted concurrently herewith as the sequence listing text file "52484A_Seqlisting.txt", file size 40,765 KiloBytes (KB), created on 20 Jul. 2020. The afore-mentioned sequence listing is hereby incorporated by reference in its entirety pursuant to 37 C.F.R. § 1.52(e)(5).

FIELD OF THE INVENTION

The invention relates to a novel anti-infective compound, the use thereof for the production of a pharmaceutical composition for the treatment and/or prophylaxis of a disease, preferably an infectious disease, a pharmaceutical composition comprising said compound, and to methods of producing said compounds.

BACKGROUND OF THE INVENTION

The control and treatment of infectious diseases is one of the biggest challenges of the modern society. Nearly 40,000 men, women and children are dying every day from infectious diseases worldwide.

RELATED PRIOR ART

Among the infectious agents pathogenic bacteria are more than ever of high relevance. Bacterial infections may be treated with antibiotics, which are intended to kill the bacteria or to prevent their growth. However, antibiotic resistance threatens the infective prevention and treatment of an ever-increasing range of pathogenic bacteria. Antibiotic resistance is present in all parts of the world. It is seen as an increasingly serious threat to global public health that requires action across all sectors of science and society.

There are high proportions of antibiotic resistance in bacteria that cause common infections in all regions of the world, e.g. urinary tract infections, pneumonia, blood stream infections. A high percentage of hospital-acquired infections are caused by so-called methicillin-resistant *Staphylococcus aureus* (MRSA). MRSA is a bacterium responsible for several difficult to-treat infections in humans. MRSA is also called oxacillin-resistant *Staphylococcus aureus* (ORSA). MRSA is any strain of *Staphylococcus aureus* that has developed, through the process of natural selection, resistance to beta-lactam antibiotics, which include the penicillins, such as methicillin, dicloxacillin, nafcillin, oxacillin etc., as well as the cephalosporins. MRSA is especially troublesome in hospitals, prisons, and nursing homes, where patients with open wounds, invasive devices, and weakened immune systems have an elevated risk of a nosocomial infection in comparison to the general public. MRSA began as a hospital-acquired infection, but has developed limited endemic status and is now increasingly community-acquired.

Besides prevention measures new ways of treatment of MRSA are subject of intensive research. According to a Henry Ford Hospital study the drug of choice for treating MRSA is now believed to be vancomycin. However, several newly discovered strains of MRSA show antibiotic resistance even to vancomycin, e.g. vancomycin-resistant *Staphylococcus aureus* (VRSA), as well as against other newly developed antibiotics intended for a treatment of MRSA.

Document DE 10 2005 055 944 discloses cyclic iminopeptide derivatives intended to be used as antibacterial agents. However, such known compounds have so far not proven their worth in the clinical practice.

SUMMARY OF THE INVENTION

Against this background it is an object underlying the invention to provide a new anti infective compound effective in the treatment of infectious agents which are resistant to currently available drugs, such as methicillin-resistant *Staphylococcus aureus* (MRSA), vancomycin-resistant *Staphylococcus aureus* (VRSA) or vancomycin-resistant Enterococci (VRE).

This object is met by the provision of a compound having the following formula (I):

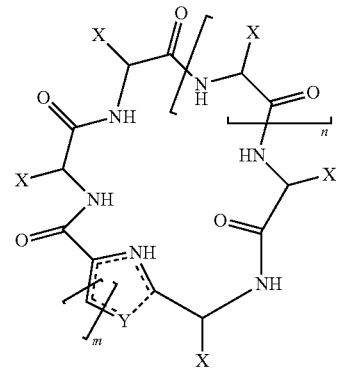

wherein
  X is selected from the group consisting of: H, CH$_3$, CH$_2$CH$_3$, anthranylalanine, DOPA, tyrosine, threonine,

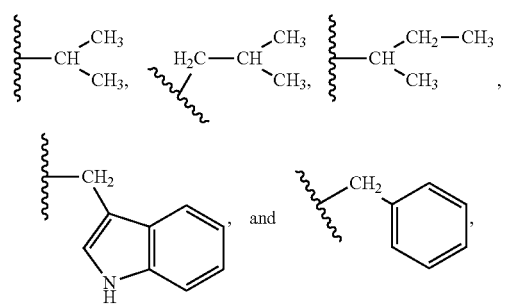

under the proviso that at least one and, preferably at most two or three, out of X is:

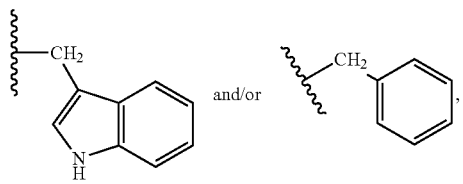 [SMILES: *Cc1c[nH]c2ccccc12 ; *Cc1ccccc1]

and

Y is selected from the group consisting of O, H, OH, S, and N, under the proviso that in

---------- represents no bond, single bond or double bond,
========== represents single bond or double bond,
m is an integer between 0 and 3,
n is an integer between 0 and 4,
and the salts thereof, the solvates thereof and the solvates of the salts thereof.

The inventors succeeded in isolating a cyclic peptide from the bacterium *Staphylococcus lugdunensis* which falls under the scope of formula (I). This cyclic peptide exhibits strong activity against various pathogenic bacteria, including the vancomycin resistant (VRE) *Enterococcus faecalis* and *E. faecium*, *Streptococcus pneumonia*, *Listeria monocytogenes*, and *Staphylococcus aureus*. In further investigations the inventors were able to identify a core structure represented by formula (I), which is responsible for the antimicrobial activity of the isolated compound.

The new compound comprises 5-9 amino acids in a cyclic configuration. In this "large ring" among the amino acids aromatic and hydrophobic amino acids are preferred, wherein at least one tryptophan or phenylalanine is required and in an embodiment preferably at most two, three, four etc. are tryptophan or phenylalanine. In an embodiment of the invention no more than two aromatic amino acids are provided.

The new compound further may comprise a "small ring", i.e. a 5-, 6- or 7-membered heterocyclic ring, such as a thiazolidine, oxazolidine, or imidazolidine ring. The small ring does not need a double bond, there can be, however, a single or double bond in the small ring as indicated by the dashed underlined line. Alternatively the "small ring" can be opened up without any ring structure as indicated by the dashed line The compound of the invention may, depending on its specific structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers. If the compound of the invention may occur in tautomeric forms, the present invention encompasses all tautomeric forms.

Salts preferred for the purposes of the present invention are physiologically acceptable salts of the compound of the invention. Also encompassed, however, are salts which are themselves not suitable for pharmaceutical applications but can be used for example for the isolation or purification of the compound of the invention.

Examples of pharmaceutically acceptable salts of the compound of formula (I) include salts of inorganic bases like ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethanolamine, diethylamine, triethylamine, ethylenediamine, procaine, morpholine, pyrroline, piperidine, N-ethylpiperidine, N-methylmorpholine, piperazine as the organic base; or salts with basic amino acids, in particular lysine, arginine, ornithine and histidine.

Examples of pharmaceutically acceptable salts of the compound of formula (I) also include salts of inorganic acids like hydrochlorides, hydrobromides, sulfates, phosphates or phosphonates; salts of organic acids, in particular acetates, formates, propionates, lactates, citrates, fumarates, maleates, benzoates, tartrates, malates, methanesulfonates, ethanesulfonates, toluenesulfonates or benzenesulfonates; or salts with acidic amino acids, in particular aspartate or glutamate.

Solvates for the purposes of the invention refer to those forms of the compound of the invention, which in the solid or liquid state form a complex by coordination with solvent molecules. Hydrates are a specific form of solvates in which the coordination takes place with water.

The compound of the invention may also be complexed, e.g. with iron, calcium, etc., in which the compound may act as a ligand, so that a corresponding complex is also subject of the present invention.

The problem underlying the invention is herewith completely solved.

According to another embodiment of the invention the compound is characterized by the following formula (II):

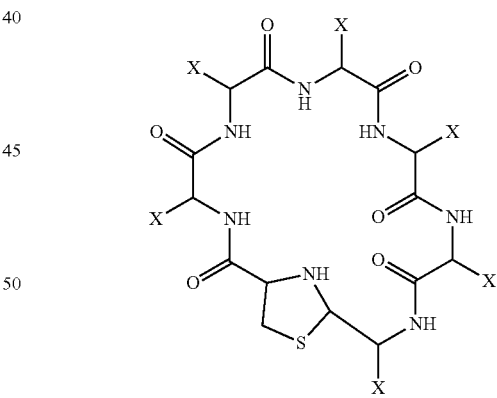

wherein
X is selected from the group consisting of: H, CH$_3$, CH$_2$CH$_3$, anthranylalanine, DOPA, tyrosine, threonine,

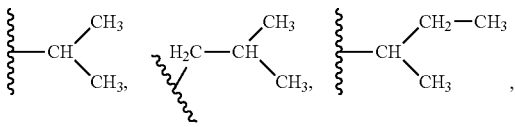

-continued

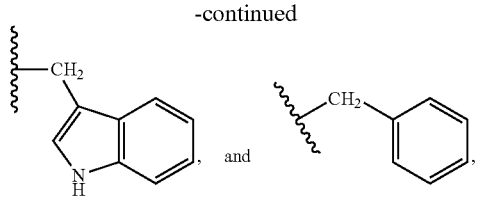

under the proviso that at least one and, preferably at most two or three, out of X is:

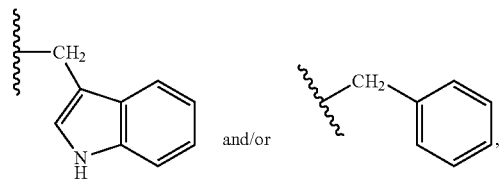 [SMILES: *Cc1c[nH]c2ccccc12 ; *Cc1ccccc1]

and the salts thereof, the solvates thereof and the solvates of the salts thereof.

As the inventors were able to demonstrate, the compound according to the invention consisting of a 7 amino acids comprising large ring and a thiazolidin small ring has particularly strong antimicrobial activities.

The features, characteristics and advantages specified for the compound represented by formula (I) apply to the compound represented by formula (II) as well.

According to another embodiment the compound according to the invention is characterized by the following formula (III):

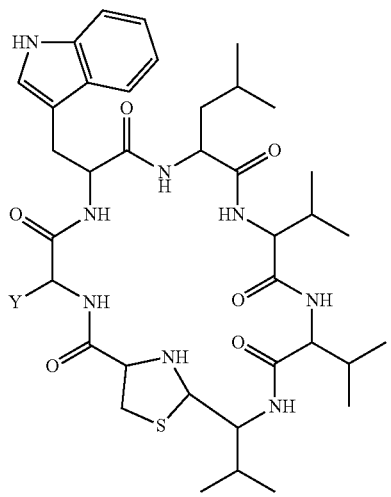

wherein
Y is selected from the group consisting of:

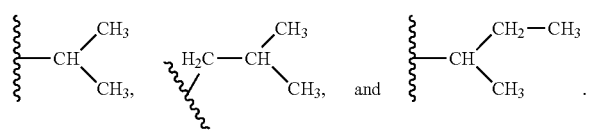

As the inventors were able to realize the compound according to the invention represented by the core structure of formula (III) exhibits a very high antimicrobial activity.

The features, characteristics and advantages specified for the compound represented by formulas (I) and (II) apply to the compound represented by formula (III) as well.

In another embodiment the compound according to the invention is characterized by the following formula (IV):

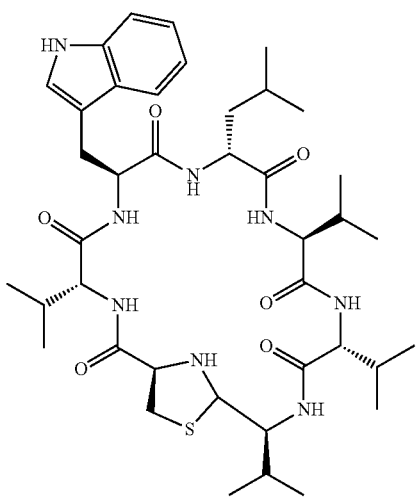 [SMILES: CC(C)C[C@H]1NC(=O)[C@H](Cc2c[nH]c3ccccc23)NC(=O)[C@@H](C(C)C)NC(=O)[C@@H]2CSC(N2)[C@H](C(C)C)NC(=O)[C@@H](C(C)C)NC(=O)[C@H](C(C)C)NC1=O]

In this embodiment the exact compound is provided that was isolated by the inventors from *Staphylococcus lugdunensis*. This compound has been exemplarily used in the embodiments to demonstrate the antimicrobial activity of compounds represented by the general formulas (I)-(III). As this has been demonstrated by the inventors, the compound has bactericidal activity, therefore ensures an effective combating of a bacterial infection. This compound can either be isolated from *Staphylococcus lugdunensis* by well-known methods of microbiology in combination with chemical chromatography or synthesized by means of peptide synthesis.

The features, characteristics and advantages specified for the compound represented by formulas (I), (II), and (III) apply to the compound represented by formula (IV) as well.

In another embodiment of the invention the compound according to the invention is provided for the treatment and/or prophylaxis of disease, preferably an infectious disease, further preferably a bacterial disease, further preferably an infection by a Gram-positive bacterium, highly preferably an infection by *Staphylococcus aureus*, especially including its methicillin-resistant (MRSA) and vancomycin-resistant *Staphylococcus aureus* (VRSA) forms.

This measure has the advantage that a compound is provided being effective against a broad range of infectious agents and in particular against *Staphylococcus aureus* in its MRSA variant, which is responsible for several serious infections in humans.

Due to its pharmacological properties the compound of the invention can be used alone or in combination with other agents for the treatment and/or prophylaxis of diseases or infectious diseases, respectively, in particularly bacterial infections.

For example, local and/or systemic diseases can be treated and/or prevented, which are caused by the following pathogens or by mixtures of the following pathogens:

Gram-positive cocci, such as Staphylococci (*Staph. aureus, Staph. epidermidis*) and *Streptococcus* (*Strept. agalactiae, Enterococcus faecalis, Strept. pneumonia, Strept. pyogenes*), Gram-positive rods, such as *Bacillus* (*anthracis*), *Listeria* (*monocytogenes*) and *Corynebacterium* (*diphteriae*), Gram-negative cocci (*Neisseria gonorrhoeae*) and Gram-negative rods, such as Enterobacteriaceae, e.g. *Escherichia coli, Haemophilus influenzae, Citrobacter* (*Citrob. freundii, Citrob. divernis*), *Salmonella* and *Shigella*, further *Klebsiella* (*Klebs. pneumoniae, Klebs. oxytoca*), *Enterobacter* (*Ent. aerogenes, Pantoea agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. In addition, the antibacterial spectrum includes the genus of *Pseudomonas* (*Ps. aeruginosa* and *Ps. maltophilia*) and strictly anaerobic bacteria such as *Bacteroides fragilis*, representatives of the genus of *Peptococcus, Peptostreptococcus* and the genus *Clostridium*; also mycoplasms (*M. pneumoniae, M. hominis, M. urealyticum*), and mycobacteria, for example *Mycobacterium tuberculosis*.

The above list of pathogens is merely to be illustrative and not limiting.

Diseases caused by the pathogens mentioned or by mixed infections which can be cured, prevented, or attenuated by the compound according to the invention are, for example:

Infectious diseases in humans such as septic infections, bone and joint infections, skin infections, postoperative wound infections, abscesses, cellulitis, wound infections, infected burns, burns, infections of the mouth, infections after dental surgery, septic arthritis, mastitis, tonsillitis, urogenital infections and eye infections.

Another embodiment of the invention relates to the use of the compound according to the invention for the treatment and/or prophylaxis of nasal colonization and infections.

According to the findings of the inventors herewith the compound is put into place at the natural environment of action of the isolated cyclic peptide.

Bacterial infections cannot only be treated or prevented in humans but also in animals. Examples are:

Pig: *coli* diarrhea, enterotoxemia, sepsis, dysentery, *salmonellosis*, metritis-mastitis-*agalactiae* syndrome, mastitis;

Ruminants (cattle, sheep, goats): diarrhea, sepsis, bronchopneumonia, *salmonellosis*, pasteurellosis, mycoplasmosis and genital infections;

Horse: bronchopneumonia, puerperal and post puerperal infections, *salmonellosis;*

Dog and cat: bronchopneumonia, diarrhea, dermatitis, otitis, urinary tract infections, prostatitis;

Poultry (chicken, turkey, quail, pigeons, aviary birds and others): mycoplasmosis, *E. coli* infections, chronic airway disease, *salmonellosis*, pasteurellosis, psittacosis.

Similarly, bacterial diseases can be treated in the breeding and keeping of utility and ornamental fish but also humans, wherein the antibacterial spectrum of the pathogens mentioned above further extends to pathogens such as *Pasteurella, Brucella, Campylobacter, Listeria, Erysipelothris, Corynebacteria, Borrelia, Treponema, Nocardia, Rikettsia, Yersinia*.

With the compound according to the invention bacterial infections cannot only be treated or prevented in humans or animals but also plants.

The compound according to the invention can act systemically and/or locally. For this purpose, it can be administered in a suitable manner, such as oral, parenteral, pulmonary, nasal, sublingual, lingual, buccal, rectal, dermal, transdermal, conjunctival, otic or associated with an implant or stent.

A topical application is especially preferred since the inventors successfully demonstrated that the compound according to the invention is able to penetrate even deeper tissue areas.

Against this background, another subject-matter of the invention is the use of the compound according to the invention for the production of a pharmaceutical composition for the treatment and/or prophylaxis of a disease, preferably an infectious disease, further preferably a bacterial disease, further preferably an infection by a Gram-positive bacterium, highly preferably an infection by *Staphylococcus aureus*, including its methicillin-resistant form (MRSA).

Another subject-matter of the present invention is a pharmaceutical composition comprising the compound according to the invention and a pharmaceutical acceptable carrier.

For this purpose, a "pharmaceutically acceptable carrier" is understood to mean any excipient, additive, or vehicle that is typically used in the field of the treatment of infectious diseases and which simplifies or enables the administration of the compound according to the invention to a living being, and/or improves its stability and/or activity. The pharmaceutical composition can also incorporate binding agents, diluting agents or lubricants. The selection of a pharmaceutical carrier or other additives can be made on the basis of the intended administration route and standard pharmaceutical practice. As pharmaceutical acceptable carrier use can be made of solvents, extenders, or other liquid binding media such as dispersing or suspending agents, surfactant, isotonic agents, spreaders or emulsifiers, preservatives, encapsulating agents, solid binding media, depending upon what is best suited for the respective dose regime and is likewise compatible with the compound according to the invention. An overview of such additional ingredients can be found in, for example, Rowe (Ed.) et al.: Handbook of Pharmaceutical Excipients, $7^{th}$ edition, 2012, Pharmaceutical Press.

According to another embodiment of the invention the pharmaceutical composition is provided for the treatment and/or prophylaxis of a disease, preferably an infectious disease, further preferably a bacterial disease, further preferably an infection by a Gram-positive bacterium, highly preferably an infection by *Staphylococcus aureus* including its methicillin resistant forms (MRSA).

The features, characteristics, advantages and embodiments of the compound according to the invention likewise apply to the use and the pharmaceutical composition according to the invention.

Another subject-matter of the present invention is a method of producing the compound according to the invention, comprising the following steps: 1. Providing bacteria of the species of *Staphylococcus lugdunensis*, 2. Purifying the compound according to the invention from said bacteria.

Herewith a method is provided, which has been used by the inventors for producing or isolating the compound according to the invention. The species of *Staphylococcus lugdunensis* referred to in this embodiments or elsewhere in the disclosure includes the isolate or strain IVK28, respectively.

In an embodiment of the method according to the invention after step (1) and before step (2) the bacteria and the medium of the bacterial culture are extracted and the bacterial and the medium extract are subjected to step (2) where the compound is purified from said bacterial and medium extract.

This measure has the advantage that only the main sources of the compound according to the invention are provided to the purifying step from which it can then be isolated by methods of microbiology in combination with chemical chromatography, which are well known to the skilled person.

In another embodiment of the method according to the invention in step (2) the purification involves the use of high performance liquid chromatography (HPLC) to identify a peak signal, which is associated with said compound.

This measure has the advantage that a well-established tool of peptide purification is used, which allows a reliable identification of the compound according to the invention.

In another embodiment of the method according to the invention said signal peak corresponds to a molecular mass of approx. 650 Da-950 Da, preferably of approx. 700 Da-850 Da, further preferably of approx. 750 Da-800 Da, further preferably of approx. 770 Da-790 Da, and highly preferably of approx. 782.5 Da.

This measure has the advantage that the compound according to the invention, which falls within the indicated ranges, can be easily identified via its molecular mass.

Another subject-matter of the present invention is a method of producing the compound according to the invention, which comprises the following steps: 1. Expressing the non-ribosomal peptide synthetase system II of the species of *Staphylococcus lugdunensis* (NRPS-II) in a biological system, 2. Incubating the expressed NRPS-II under conditions allowing the synthesis of the compound according to the invention, 3. Purifying said compound.

The inventors were able to find out that the NRPS-II of the species of *Staphylococcus lugdunensis* is responsible for the synthesis of the compound according to the invention and, therefore, this method makes use of the natural apparatus for producing the new compound.

In an embodiment of the method according to the invention said NRPS-II is encoded by a nucleic acid molecule comprising any of the coding sequences of the genes lugA, lugB, lugC, lugD, and, optionally, of a transcriptional regulator of GntR family, ABC transporter (GdmF type multidrug transport system), ABC-2 type transport system permease protein, ABC transporter, hyp. membrane protein, TetR/AcrR family regulator, thioesterase family protein, 4'-phosphopantetheinyltransferase, and put. negative regulator of sigY (in *Bacillus*).

The inventors were able to identify the genes responsible for the synthesis of the compound according to the invention and the optional co-factors, and, therefore, provide a method where the essential features are used in a molecular biological artificial system to generate the compounds in a large scale.

The coding sequences comprised by the NRPS-II can be taken from SEQ ID NO: 1; the nucleotide positions are indicated in the following:

lugA: 6007-13131
lugB: 13121-17341
lugC: 17359-26172
lugD: 26893-28632
transcriptional regulator of GntR family: 427-936
ABC transporter (GdmF type multidrug transport system): 1253-2143
ABC-2 type transport system permease protein: 2140-2904
ABC transporter: 2917-3630
hyp. membrane protein: 3623-5164
TetR/AcrR family regulator: 5409-5981
Thioesterase family protein: 26169-26855
4'-phosphopantetheinyltransferase: 28640-29293
put. negative regulator of sigY (in *Bacillus*): 1027-1266

Against this background, another subject-matter of the present invention is a nucleic acid molecule comprising the nucleotide sequence of SEQ ID NO: 1 and/or any of the before-listed coding sequences of the non-ribosomal peptide synthetase system II of the species of *Staphylococcus lugdunensis* (NRPS-II). Examples for such nucleic acid molecules include vectors or plasmids configured for a controlled expression of the encoded proteins in common molecular biological expression systems. Subject of the invention is also a nucleic acid molecule encoding the identical protein and/or peptide as encoded by the before mentioned nucleic acid molecule, however having a modified or different nucleotide sequence due to the degeneration of the genetic code.

Another subject-matter of the invention relates to the products generated by the expression of the nucleic acid molecule according to the invention, including proteins and/or peptides encoded by any of the genes lugA, lugB, lugC, lugD, transcriptional regulator of GntR family, ABC transporter (GdmF type multidrug transport system), ABC-2 type transport system permease protein, ABC transporter, hyp. membrane protein, TetR/AcrR family regulator, thioesterase family protein, 4'-phosphopantetheinyl-transferase, and put. negative regulator of sigY (in *Bacillus*), or encoded by before mentioned nucleotide sequence which are itself subject-matter of the present invention.

A further subject-matter of the invention relates to an antibody specifically directed against any of the products (peptides, proteins) generated by the expression of the nucleic acid molecules according to the invention.

In another embodiment of the method according to the invention the conditions allowing the synthesis of the compound according to the invention comprise amino acids, thioesterase, and buffer.

By this measure the conditions are adjusted in a way, which ensures a high yield of the compound according to the invention.

Another object of the present invention is a method for the treatment and/or prophylaxis of diseases, especially of the aforementioned diseases, in a living being, such a human or animal being, comprising the administration to said living being of an antibacterially effective amount of the compound according to the invention.

Another object of the invention is a probiotic comprising a microorganism capable of producing the compound according to the invention.

The inventors have surprisingly realized that a micororganism, such as a bacterium, producing the novel antibacterial compound can be directly used, e.g. to prevent or reduce the growing or colonization by a pathogenic microorganism of an organ of a living being.

According to the invention, a "probiotic" is to be understood as a microorganism which provides health benefits to a living being, such as a human being, when consumed or administered. In particular, the administration of the probiotic to an organ susceptible of being colonized by a pathogen microorganism, such as *Staphylococcus aureus*, will result in a displacement of such pathogenic agent. This results in a reduction of the pathogenic burden or even in a complete elimination.

In another embodiment the microorganism is *Staphylococcus lugdunensis*. *Staphylococcus lugdunensis* can be used in its natural form, i.e. as the wild type, or as a modified form, e.g. a genetically modified form or an attenuated wild type variant, however still producing the compound according to the invention.

In another embodiment of the invention the probiotic is used for preventing or reducing the colonization by a pathogenic microorganism of an organ of a living being, e.g. a human being. The organ may be the nose, wherein the probiotic may then be administered into the nose of the living being, or it may be the skin, wherein the probiotic may then be administered onto the skin of the living being.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention.

The features mentioned in the specific embodiments are also features of the invention in general, which are not only applicable in the respective embodiment but also in an isolated manner in the context of any embodiment of the invention.

The invention is also described and explained in further detail by referring to the following drawings

BRIEF DESCRIPTION OF THE DRAWINGS

FIG. 3A shows HPLC-UV chromatogram ($UV_{210\ nm}$) of cell extracts of S. lugdunensis wild type (blue) and mutant M1 (red) (x-axis: time [min], y-axis adsorption at 210 nm [mAU]; FIG. 3B shows HPLC-MS of the peak at 10.6 min retention time resulting in a mass of 782.5 Da (ESI pos.: m/z 783.6 $[M+H]^+$, ESI neg.: m/z 781.5 $[M-H]^-$, m/z 817.5 $[M+Cl]^-$);

FIG. 6A shows a killing curve. Incubation of S. aureus with a 10×MIC of lugdunin leads to complete killing of the inoculum after 30 h. Data represent medians±S.D. of three independent experiments. FIG. 6B shows serial passaging of S. aureus with sub-inhibitory concentrations of rifampicin leads to rapidly increasing spontaneous resistance against rifampicin. However, such resistance development was not observed with lugdunin. A representative of two independent experiments is shown.

FIG. 8: shows that lugdunin is active in vivo in a mouse tape-stripping model. After colonization of shaved C57BL/6 mouse skin with S. aureus Newman lugdunin was applied three times in a few hours distance. After 45 hours mice were sacrificed and the numbers of bacteria were determined on the skin surface (wash fraction) and in the deeper skin tissue (scrape fraction). Treatment with lugdunin significantly reduced the bacterial load in both fractions indicating its efficacy also in vivo. (* $p<0.05$);

FIG. 10A shows S. aureus is overgrown by S. lugdunensis IVK28 wild type on agar plates inoculated at ratios of ~90:10. In contrast, FIG. 10B shows IVK28 ΔlugD is overgrown by S. aureus at ratios of ~90:10 (b). FIG. 10C shows the capacity of S. lugdunensis ΔlugD to overgrow S. aureus is largely restored by plasmid-encoded lugD. FIG. 10D shows S. aureus overgrows IVK28 ΔlugD even when inoculated in ratios of ~10:90. Data represent mean values±S.D. of three independent experiments. Significant differences between starting conditions and indicated time points were analysed by one-way ANOVA (*, $p<0.05$; , $p<0.01$; *, $p<0.001$; ****, $p<0.0001$; n.s, not significant). FIG. 10E shows cotton rat noses co-colonised by S. aureus and S. lugdunensis IVK28 wild type show significantly less S. aureus CFUs after five days compared to S. lugdunensis IVK28 ΔlugD. Horizontal lines represent the median of each group. Significant differences, calculated by the Mann Whitney test, are indicated (*, $p<0.05$).

DESCRIPTION OF PREFERRED EMBODIMENTS

A. Methods

1. Strains and Growth Conditions

Figure 1:
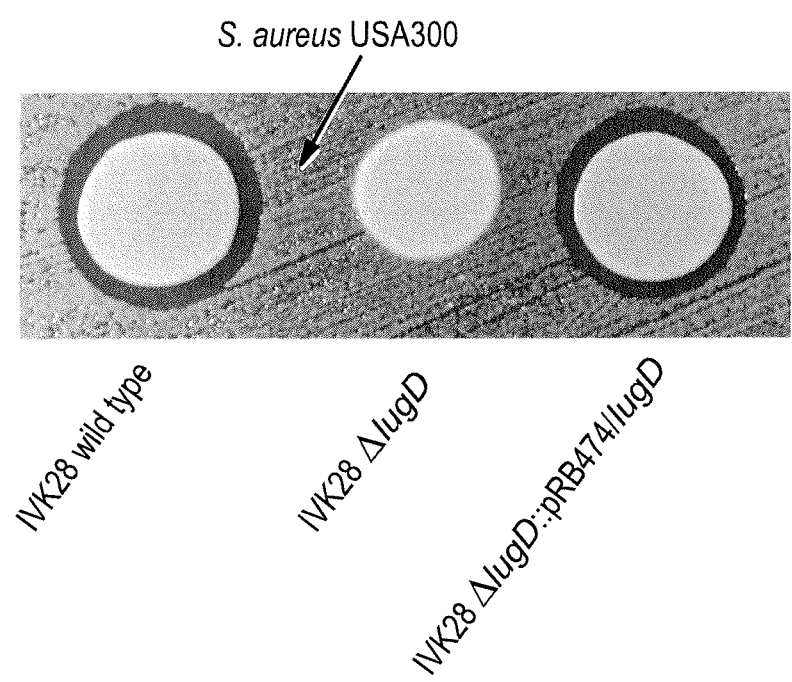
FIG. 1 shows the lugdunin production by S. lugdunensis wild type and isogenic mutants. Bioactivity assay with the S. lugdunensis IVK28 wild type, the ΔlugD mutant and the complemented mutant against S. aureus USA300. BM plates were inoculated with a lawn of S. aureus USA300. Hereon S. lugdunensis IVK28 cells from overnight cultures of the wild type, the mutant ΔlugD and the complemented mutant ΔlugD::pRB474/lugD were spotted.

The Staphylococcus strains used in this study were S. aureus USA300 LAC, S. aureus USA300 NRS384, S. aureus Mu50, S. aureus RN4220, S. aureus SA113, S. aureus Newman, S. aureus PS187, S. lugdunensis IVK28, S. lugdunensis IVK28 ΔlugD, S. lugdunensis IVK28 ΔlugD::pRB474/lugD, and S. lugdunensis IVK28-Xyl. Further strains used for MIC determination were Enterococcus faecium BK463, E. faecalis VRE366, Listeria monocytogenes ATCC19118, *Streptococcus pneumoniae* ATCC49619, *Pseudomonas aeruginosa* PAO1, and *Escherichia coli* DH5a. *E. coli* DC10B was used as the cloning host. In addition, a set of 60 *S. aureus* and 17 *S. lugdunensis* strains were isolated from diagnostic samples in the course of the colonisation study described below.

Basic medium (BM: 1% soy peptone, 0.5% yeast extract, 0.5% NaCl, 0.1% glucose and 0.1% $K_2HPO_4$, pH 7.2) was used as the standard growth medium. MIC determinations and killing assays were performed in Mueller Hinton Broth (MHB; Roth, Karlsruhe, Germany). For the identification of *S. lugdunensis*, selective *S. lugdunensis* medium (SSL) was used as previously described in the art. When necessary, antibiotics were used at concentrations of 250 µg/mL for streptomycin, 10 µg/mL for chloramphenicol, 2.5 µg/mL for erythromycin and 100 µg/mL for ampicillin.

2. Bioactivity Test

The anti-*S. aureus* activity of *S. lugdunensis* IVK28 was identified by screening 90 nasal staphylococcal isolates for the capacity to inhibit growth of *S. aureus*. For this purpose BM agar was inoculated 1:10,000 with an overnight culture of *S. aureus* USA300 LAC. The test strains were inoculated on the resulting bacterial lawn, and the plates were incubated for 24-48 h at 37° C. To investigate the production of antimicrobial activity by IVK28 under iron-limiting conditions, BM agar was supplemented with 200 µM 2, 2'-bipyridine.

3. Transposon Mutagenesis and Elucidation of the Lugdunin Gene Cluster

The temperature-sensitive plasmid pTV1ts, which contains the 5.3-kb transposon Tn917 ($erm^R$) from *E. faecalis*, was transferred into *S. lugdunensis* IVK28 by electroporation. Transposition mutants were screened for loss of antimicrobial activity against *S. aureus*. Chromosomal DNA was isolated by standard procedures from non-inhibitory clones, and the primers Tn917 up and Tn917 down (Extended Table 2) were used to directly sequence the flanking regions of the transposon insertion site. Sequence analysis was performed with DNASTAR Lasergene software (DNASTAR Inc., Madison, Wis., USA). Bioinformatic analysis was performed by BLAST® and antiSMASH 3.0.

4. Generation of *S. lugdunensis* IVK28-Xyl

The flanking regions of lugR were amplified by PCR with the primer pairs SlPr1-up/SlPr1-down and SlPr2-up/SlPr2-down. The plasmid pBASE6-erm/lox 1, a derivative of pBASE6, already containing an erythromycin resistance cassette in the singular SmaI site, was linearized with Acc65I. The identically digested SlPr1 PCR product, containing one natural Acc65I restriction site and one introduced by the primer, was ligated into pBASE6-erm/lox1. The resulting vector with the correctly oriented SlPr1 PCR product and the SlPr2 PCR product were ligated after digestion with EcoRV and BglII. The resulting pBASE6-erm/lox 1 construct with both flanking regions inserted was linearized with BssHII, treated with Klenow enzyme and digested with BglII. The required xylR fragment with the downstream-located xy/AB-promoter was excised from pTX15 by HindIII restriction treatment with Klenow enzyme and subsequent digestion with BamHI. The ligation of the xylR fragment into the appropriate vector generated pBASE6-erm/lox1-xylR, which was transferred into *E. coli* DC10B and subsequently into *S. aureus* PS187. The resulting plasmid pBASE6-erm/lox1-xylR was transduced into *S. lugdunensis* IVK28 via the bacteriophage φ187. Homologous recombination for replacement of lugR by erm/xylR was performed, as previously described in the art, generating the xylose-inducible lugdunin producer strain *S. lugdunensis* IVK28-Xyl.

5. Production and Purification of Lugdunin

A fresh overnight culture of *S. lugdunensis* IVK28-Xyl was inoculated 1:1,000 in BM without glucose and was supplemented with 0.5% xylose. After incubation at 37° C. under continuous shaking (160 rpm) for 24 h, whole cultures were extracted with 1-butanol at a ratio of 5:1. The aqueous phase was discarded, and the organic phase was evaporated at 37° C. under reduced pressure and finally dissolved in methanol. The methanol extract was applied to a gel filtration column (Sephadex LH20, 1.6×80 cm, flow rate 1 mL/min). The active fractions containing lugdunin were pooled, evaporated at 37° C. under reduced pressure and dissolved in dimethyl sulfoxide (DMSO). This solution was then subjected to a preparative reverse-phase HPLC column (Kromasil C18, 7 µm, 250×20 mm; Dr. Maisch, Ammerbuch, Germany) with an isocratic elution at 79% methanol in water for 20 min. The peak containing lugdunin was baseline-separated from the remaining compounds, and methanol was evaporated at 37° C. under reduced pressure to yield a white powder of pure lugdunin.

6. Chemical Synthesis of Lugdunin and Lugdunin Derivatives

Total chemical synthesis was achieved by Fmoc (9-fluorenylmethoxycarbonyl) strategy based manual solid-phase peptide synthesis and was established on an H-Val-H NovaSyn® TG resin (Novabiochem, Switzerland). Amino acids were coupled in a four-fold excess using HATU (1-[Bis(dimethylamino)methylene]-1H-1,2,3-triazolo[4,5-b]pyridinium 3-oxid hexafluorophosphate). Valine positions were coupled twice by use of PyOxim ([Ethyl cyano(hydroxyimino)acetato-$O^2$]tri-1-pyrrolidinylphosphonium hexafluorophosphate) for the second coupling instead of HATU. Peptides were cleaved from the resin with acetonitrile/water/trifluoroacetic acid (79.95/20/0.05) for 30 min. Lyophilization overnight yielded the crude product. Crude synthetic lugdunin products were purified by RP-HPLC and compared with the natural product by HR-LC-ESI-MS, additional chiral-HPLC methods (column: Dr. Maisch Reprosil Chiral NR, Ammerbuch, Germany; elution with 80% premixed methanol in $H_2O$ at 1.5 mL/min flow rate), bioactivity assay and advanced Marfey's analysis.

7. MIC Assay and Spectrum of Activity

*S. aureus* RN4220, *S. aureus* USA300 (LAC), *S. aureus* USA300 (NRS384), *S. aureus* SA113, *S. aureus* Mu50, *E. coli* DH5a and *P. aeruginosa* PAO1 were grown overnight in MHB. *E. faecalis* VRE366, *E. faecium* BK463, *S. pneumoniae*, and *L. monocytogenes* were grown in tryptic soy broth (TSB: Difco Laboratories, Augsburg, Germany). All strains were incubated at 37° C. under continuous shaking. Early log-phase grown bacteria were adjusted in MHB to $1\times10^6$ cells/well in microtiter plates (MTP), mixed with varying concentrations of the antibiotic and incubated at 37° C. for 24 h under continuous shaking. The $OD_{600}$ of each well was measured with a microplate reader, and the lowest peptide concentrations, which displayed no bacterial growth, were defined as the MIC. The assays were performed in 96-well microtiter plates.

8. Killing Assay

Fresh MHB was inoculated 1:10,000 with an overnight culture of *S. aureus* USA300 LAC and was incubated at 37° C. under continuous shaking (160 rpm) until bacteria were grown to $1\times10^6$ cells/mL. Then, 10×MIC lugdunin was added. At the time points 0 h, 2 h, 4 h, 8 h, 24 h and 30 h, samples were taken and centrifuged. The pellet was resuspended in 1×PBS and serially diluted. The dilutions were spotted on tryptic soy agar, and colony counts were determined after overnight incubation at 37° C. To determine cell numbers <$10^2$ cells/mL, whole cultures of 1 mL were centrifuged and plated on TSA.

9. Cytotoxity Against Human Neutrophil Granulocytes

Human neutrophil granulocytes were freshly isolated from the blood of healthy volunteers by standard Histopaque/Ficoll centrifugation. The lysis of neutrophil granulocytes was monitored by the release of the enzyme lactate dehydrogenase (LDH). Lugdunin was added at final concentrations of 50, 25 and 12.5 µg/mL in 0.5% DMSO to wells of a 96 well tissue culturing plate containing 1×$10^6$ neutrophil granulocytes per well in 2004 RPMI-1640 medium (2 g/l $NaHCO_3$, 10% foetal calf serum, 1% L-glutamine and 1% penicillin-streptomycin, PAN Biotech) without phenol red. The plates were incubated at 37° C. and 5% $CO_2$ for 3 h and the lysis was determined with a Cytotoxicity Detection Kit (Roche Applied Sciences, Mannheim, Germany). As a positive control for high cytotoxicity, 2% Triton X-100 was added to the samples.

10. Resistance Development Study

MIC assays for the antibiotics used in this study were performed as described above. The inventors determined 1×MICs of 0.01 µg/mL rifampicin and 1.5 µg/mL lugdunin against *S. aureus* USA300. Fresh MHB was inoculated 1:10,000 with an overnight culture of *S. aureus* USA300 LAC and was incubated at 37° C. under continuous shaking. Cells were grown to early log phase, adjusted to 1×$10^6$ cells/mL, and dispensed into 96-well MTPs with 100 µL per well. Lugdunin and rifampicin were added at concentrations of 0.25×MIC, 0.5×MIC, 1×MIC, 1.5×MIC, 2×MIC and 4×MIC. After 24 h incubation at 37° C. under continuous shaking, growth was determined with a microplate reader at an $OD_{600}$ and cells from the second highest concentration of 0.25×MIC, 0.5×MIC, 1×MIC, 1.5×MIC, 2×MIC and 4×MIC from the appropriate antibiotic.

11. Statistical Analyses

Statistical analysis was performed by using GraphPad Prism (GraphPad Software, Inc., La Jolla, USA; version 5.04). Statistically significant differences were calculated by using appropriate statistical methods as indicated. For the human study, risk of nasal colonisation with *S. aureus* under the presence and absence of *S. lugdunensis*, as well as the respective point estimates of the risk ratio and confidence intervals, were determined using Stata version 12.0 (Stat Corp., College Station, Tex., USA). P values of 13.05 were considered significant.

12. Animal Models and Ethics Statement

All animal experiments were conducted in strict accordance with the German regulations of the Gesellschaft für Versuchstierkunde/Society for Laboratory Animal Science (GV-SOLAS) and the European Health Law of the Federation of Laboratory Animal Science Associations (FELASA) in accordance with German laws after approval (protocol HT1/12 for mouse skin infection and T1/10 for cotton rat colonisation) by the local authorities (Regierungspraesidium Tuebingen). All, animal and human studies, were carried out at the University Hospital, Tuebingen, and conformed to institutional animal care and use policies. No randomization or blinding was necessary for the animal infection/colonisation models, and no samples were excluded. Animal studies were performed with female C57BL/6 mice, 6-8 weeks old and cotton rats of both genders, 8-10 weeks old, respectively. The human nasal colonization study was approved by the ethics committee of the medical faculty of the University Hospital Tuebingen (project number 577/2015A).

13. Skin Infection of C57BL/6 Mice

A streptomycin-resistant *S. aureus* Newman strain was used to infect C57BL/6 mice epicutaneously by the tape stripping technique. TSB with 500 µg/mL streptomycin was inoculated 1:10,000 with a fresh overnight culture of the test strain and was incubated at 37° C. under continuous shaking until an $OD_{600}$=0.5 was reached. Cells were harvested, washed twice with 1×PBS, and adjusted to 1×$10^8$ cells/mL. The integrity of the shaved skin of the mice was affected by repeated (seven times) vigorous tape stripping to enable *S. aureus* Newman infection. An inoculum of 154 from the bacterial suspension was added to 7-mm filter paper discs, placed onto the prepared skin with two discs per animal, and covered with Finn chambers on Scanpor tape (Smart Practise, Phoenix, Ariz., USA). Finn chamber fixation occurred via Fixomull stretch plasters (BSN medical GmbH, Hamburg, Germany). After incubation for 24 h, the Finn chambers were removed and 1.5 µg of lugdunin per colonised area was applied, followed by a second and third treatment with the same amount of lugdunin after 30 h and 42 h. Six hours after the final application, mice were euthanized, the skin was large-scale detached and 4-mm punches of the originally colonised areas were vortexed in 1×PBS for 30 seconds to remove the attached bacteria from the skin (wash fraction). The skin was dissected with a scalpel to expose bacteria from deeper areas of the skin (tissue fraction), which was homogenized by vortexing in 1×PBS for 30 seconds. CFUs of both fractions were determined by serial dilutions in 1×PBS, which were then spotted onto TSA, supplemented with streptomycin, for *S. aureus* Newman$^{strep}$ specific selection. The plates were incubated overnight at 37° C.

14. Generation of *S. lugdunensis* ΔluqD and Complementation

For the construction of a marker-less knock-out strain, 1-kb flanking regions of lugD were amplified by PCR with the primer pairs lugD upstream-SacI/lugD upstream-Acc65I and lugD downstream-Acc65I/lugD downstream-BglII. The fragments were digested according to their introduced restriction sites and were ligated into the plasmid pBASE6 generating pBASE6-ΔlugD, which was transferred into *E. coli* DC10B. The correct plasmid was transferred to *S. aureus* PS187 by electroporation, which was then infected with the bacteriophage φ187 for the transduction of pBASE6-ΔlugD into the *S. lugdunensis* IVK28 wild type. The knockout was generated by homologous recombination of the flanking regions into the genome, and deletion of lugD was confirmed by PCR. For the complementation of the mutant, lugD was amplified by the primer pair lugD comp. forw-PstI/lugD comp. rev-Acc65I, digested with the appropriate restriction enzymes and ligated into identically digested pRB474. The constructed pRB474-lugD was transduced into *S. lugdunensis* IVK28 ΔlugD, as described for the knock-out mutant.

15. Competition Assay

*S. lugdunensis* IVK28 wild type, *S. lugdunensis* IVK28 ΔlugD, *S. lugdunensis* IVK28 ΔlugD::pRB474-lugD, and a streptomycin-resistant *S. aureus* Newman were grown in BM overnight at 37° C. under continuous shaking. These strains were then adjusted to 1×$10^9$ cells/mL in 1×PBS and diluted 1:10. For the starting condition of 90% *S. aureus*, equal volumes of 1×$10^9$ *S. aureus* cells/mL and 1×$10^8$ *S. lugdunensis* cells/mL were mixed. Co-cultures with only 10% *S. aureus* were also performed, and 20 µL of these mixtures were spotted in triplicate on BM agar and incubated at 37° C. Samples were taken at 0 h, 24 h, 48 h and 72 h by scraping cells from the agar plates and suspending them in 1×PBS. Serial dilutions of these samples were plated on BM and BM containing streptomycin for selection of *S. aureus*. After overnight incubation at 37° C., colony counts were determined, and the bacterial ratios of *S. aureus* and *S. lugdunensis* were calculated.

16. Co-Colonisation of Cotton Rat Noses

For the colonisation of cotton rat noses, spontaneous streptomycin-resistant mutants of *S. lugdunensis* IVK28 wild type and *S. lugdunensis* IVK28 ΔlugD were selected on BM agar plates containing 250 µg/mL streptomycin. Co-colonisation was conducted with *S. aureus* Newman$^{strep}$. The cotton rat model was described earlier. Since the capacity of *S. lugdunensis* to colonize cotton rat nares has not been studied before, the inventors determined the inoculum required for stable colonization by IVK28 wild type and its mutant ΔlugD over 5 days. The inventors' previous studies have shown that for *S. aureus* an inoculum of $10^7$ bacteria per nose results in a constant colonization of about $10^3$ CFUs per nose. To achieve a comparable colonization level with *S. lugdunensis*, an inoculum of $10^8$ bacteria per nose was required, and there was no detectable difference in colonization efficiency between wild type and ΔlugD. Therefore, co-colonization experiments in cotton rat noses were performed with 10-fold more *S. lugdunensis* than *S. aureus* to obtain a 1:1 colonization ratio.

Cotton rats were anesthetized and instilled intranasally with mixtures of either 1×10$^8$ *S. lugdunensis* wild type/1× 10$^7$ *S. aureus* Newman or 1×10$^8$ *S. lugdunensis* ΔlugD/1× 10$^7$ *S. aureus* Newman. Five days after bacterial instillation, the animals were euthanized, and noses were surgically removed. The noses were heavily vortexed in 1 mL of 1×PBS for 30 s. Dilutions of the samples in PBS were plated on SSL agar containing 250 µg/mL streptomycin to select for the used strains and to separate *S. aureus* (yellow) and *S. lugdunensis* (purple) by colour. The plates were incubated for two days under anaerobic conditions (anaerobic jar with Anaerocult® A, MerckKGaA), for the specific detection of ornithine decarboxylase activity. *S. aureus* Newman CFUs were determined afterwards. All animals received drinking water with 2.5 mg/mL streptomycin continuously, starting three days prior to the experiment, to reduce the natural nasal flora.

17. Human Colonisation Study

A total of 187 nasal swab samples from hospitalized patients were received from the diagnostics laboratory of the Institute of Medical Microbiology and Hygiene (University Clinic Tuebingen, Germany). Dilutions from each sample were plated on blood agar and SSL agar for a phenotypic identification of *S. aureus* and *S. lugdunensis*. Identity was confirmed by coagulase test and matrix-assisted laser desorption/ionization-time-of-flight mass spectrometry (Mass spectrometer: AXIMA Assurance, Shimadzu Europa GmbH, Duisburg, Database: SARAMIS™ with 23.980 spectra and 3.380 super-spectra, BioMérieux, Nuertingen).

B. Results

1. *Staphylococcus lugdunensis* Produces a Highly Potent Antimicrobial Cyclic NRPS-Peptide with Strong Activity Against *Staphylococcus aureus*

In natural habitats, especially in nutrient-poor ecological niches like the human nose [Krismer et al. (2014) Nutrient limitation governs *Staphylococcus aureus* metabolism and niche adaptation in the human nose. PLoS Pathog 10: e1003862], a fierce competition about available nutrients between colonizing bacteria is assumed. The inventors screened bacterial isolates from nasal swabs for the production of compounds active against *S. aureus*. Beside activities against a huge range of various nasal bacteria the inventors identified two strains with inhibiting properties against *S. aureus*. Whereas one isolate, which was identified as *Staphylococcus epidermidis*, exhibited constant production of the antibacterial activity under the investigated conditions, the second isolate, *Staphylococcus lugdunensis* IVK28 was found to have a particularly strong capacity to prevent the growth of *S. aureus* (FIG. 1). IVK28 showed its antibacterial effect only under iron-limiting conditions. No such inhibitory activity has been described yet for staphylococci. For this reason, this IVK28 designated isolate of *S. lugdunensis* was further investigated by the inventors.

2. The Genetic Organization of the *S. lugdunensis* IVK28 NRPS-Operon

Subsequent transposon mutagenesis of the strain resulted in the production-negative mutant M1. Analysis of the insertion site by inverse PCR resulted in the identification of a gene encoding a non-ribosomal peptide synthetase (NRPS; position 860375/76 in the annotated genome sequence of *S. lugdunensis* N920143; Acc. no: FR870271.1) which is part of the NRPS-II designated system. This clearly indicated that a small peptide might exhibit the antibacterial activity of *S. lugdunensis* against *S. aureus*. In the *S. lugdunensis* genome three putative NRPS-systems have been identified [The entire genome sequence of *Staphylococcus lugdunensis* N920143 is published in Heilbronner, et al. (2011) Genome sequence of *Staphylococcus lugdunensis* N920143 allows identification of putative colonization and virulence factors. FEMS Microbiol Lett 322: 60-67, which is incorporated herein by reference]. Whereas NRPS-I exhibits high homologies to the *S. aureus* NRPS dipeptide system encoding aureusimine A and B [Wyatt et al. (2010) *Staphylococcus aureus* nonribosomal peptide secondary metabolites regulate virulence. Science 329: 294-296] [Erratum in Science, 2011 Sep. 9; 333(6048):1381], and NRPS-III has striking similarities to described siderophore systems (Heilbronner et al., cit loc.) nothing is known about the potential product encoded by NRPS-II. Investigation of the published genomes of *S. lugdunensis* (completed sequences of strains N920143, HKU09-01 and partial sequences of strains VCU139 and M235909 (can easily determined on the basis of the genome sequence of *Staphylococcus lugdunensis* N920143. HKU09-01: between 864800/864801) showed that the applying NRPS-II operon is present in every strain sequenced so far and therefore does not depict a strain specific feature. Nevertheless, the published genomes do contain various potential sequencing errors or real frame-shift mutations, leading to different annotations. For this reason, all relevant positions, indicating a potential frame-shift, were amplified by PCR from strain IVK28. Subsequent sequencing of the PCR products revealed that the sequence of IVK28 corresponds to that of strain N920143 and its annotation, except for the annotated nucleotide position 863515 which is located at the 3'-end of gene SLUG_08110. In contrast to N920143, in IVK28 there is a stretch of eight instead of seven adenosine-nucleotides, leading to the fusion of genes SLUG_08110 and SLUG_08120 to one open reading frame.

Figure 2:
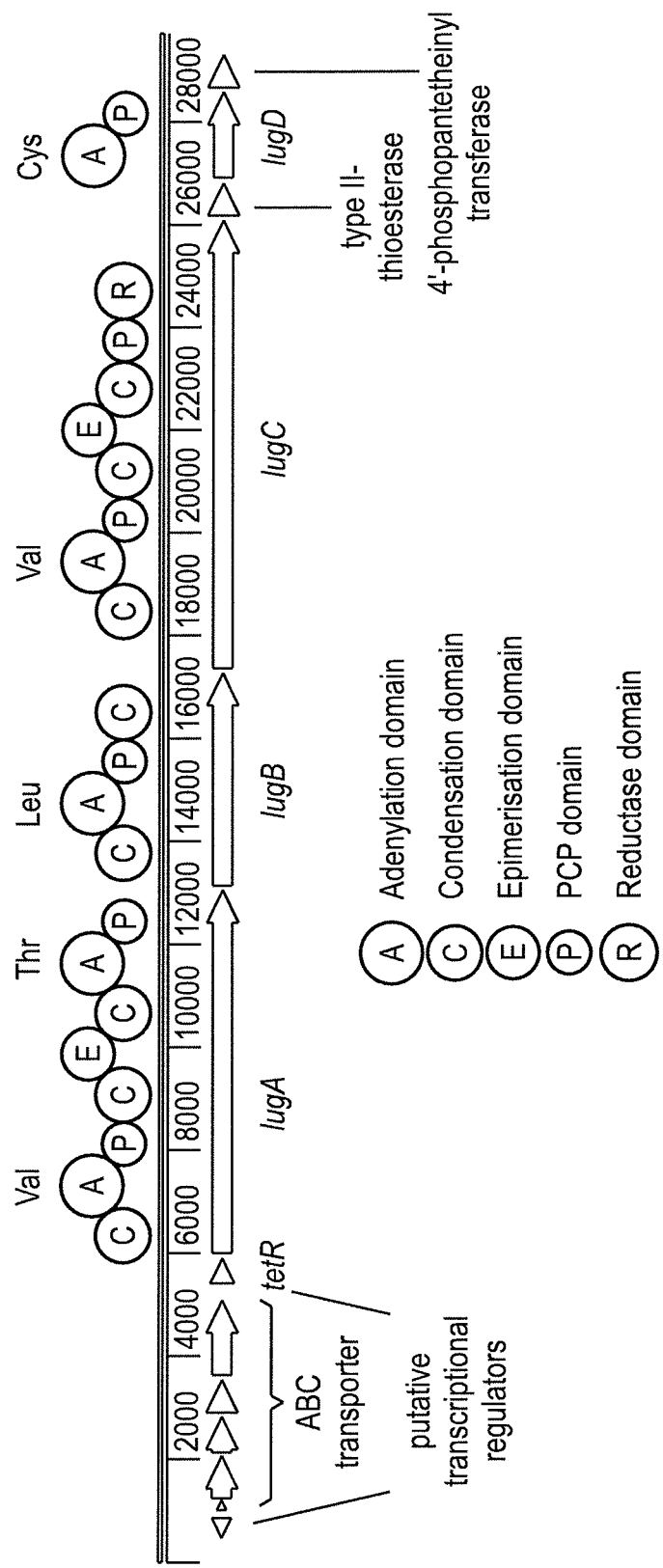
FIG. 2 shows the genetic locus required for the synthesis of lugdunin and the domain architecture of the S. lugdunensis IVK28 non-ribosomal peptide synthetases with predicted specificities.

FIG. 2 depicts the genetic organization of the 29.6 kb NRPS-II operon in *S. lugdunensis* IVK28. The locations of the coding sequences are indicated in the following sequence information of the *S. lugdunensis* IVK28 NRPS-operon:

```
         LOCUS nrp-operon IVK28 29605 bp DNA linear
FEATURES     Location/Qualifiers
misc_feature complement(427..936)
             /note="transcriptional regulator of GntR family."
misc_feature 1253..2143
             /note="ABC transporter (GdmF type multidrug
             transport system)"
misc_feature 2140..2904
             /note="ABC-2 type transport system permease protein"
misc_feature 2917..3630
             /note="ABC transporter"
misc_feature 3623..5164
             /note="hyp. membrane protein"
misc_feature 5409..5981
             /note="TetR/AcrR family regulator"
misc_feature 6007..13131
                /note="lugA" (corresponds to SLUG_08100 of
             Staphylococcus lugdunensis N920143)
misc_feature 13121..17341
                /note="lugB" corresponds to the fused sequence of
             SLUG_08110 and SLUG_08120 (by insertion of one
             additional nucleotide) of Staphylococcus
             lugdunensis N920143)
misc_feature 17359..26172
                /note="lugC" corresponds to SLUG_08130 of
             Staphylococcus lugdunensis N920143)
misc_feature 26169..26855
                /note="Thioesterase family protein"
misc_feature 26893..28632
                /note="lugD" corresponds to SLUG_08150 of
             Staphylococcus lugdunensis N920143)
misc_feature 28640..29293
             /note="4'-phosphopantetheinyltransferase"
misc_feature 1027..1266
                /note="put. negative regulator of sigY (in Bacillus)"
misc_feature 10338..10347
             /note="Tn917 insertion site"
BASE COUNT   11616 a     3273 c     4650 g     10066 t
```

Interestingly, with only 26.7% the GC-content of the NRPS-operon is significantly lower than the overall GC-content of the genome (33.8%), indicating horizontal gene transfer from an extremely low GC-organism. The operon contains four consecutive genes (named lugA, B, C, D) encoding NRPS proteins, interrupted by a type II thio-esterase gene between lugC and lugD. In the 5'-region two ABC-transporters and two potential regulatory genes are encoded. At the 3'-end of the operon the 4'-phosphopanteth-einyl-transferase is encoded. Although the antimicrobial activity could only be detected under iron-limited conditions, no obvious fur-box could be identified within the operon, indicating a rather indirect effect of lack of iron on the expression of the operon.

This so-called lug operon was exclusively found in *S. lugdunensis* and encodes a unique combination of antibiotic biosynthesis enzymes, all with less than 35% identity to any other described enzyme, suggesting that it may be responsible for biosynthesis of a novel compound. To confirm that the lug operon is responsible for the antimicrobial activity of IVK28, the smallest NRPS gene, lugD, was deleted by gene replacement. The mutant ΔlugD showed no detectable antimicrobial activity, but the phenotype was restored by complementation with a plasmid-encoded copy of lugD (FIG. 1).

Computational analysis (NRPS predictor 2, Anti-Smash, HMMER) of the proteins encoded by lugA-D revealed an uncommon domain architecture, which is shown in FIG. 2. Most NRPS-systems assemble activated amino acids in a linear fashion until product release, which is usually catalyzed by a type I thioesterase. In contrast, the *S. lugdunensis* operon exhibits a putative reductase domain for final product release, encoded at the end of the lugC. At the same time, differing from LugA-C, LugD lacks a condensation domain, which is a common feature for so called initiation modules that provide the first amino acids in some NRPS systems. The subsequent condensation reaction is then catalyzed by one of the elongation modules.

Adenylation-domain specificity prediction with the NRPS predictor2 and Anti-Smash software gave valine and threonine (LugA), leucine (LugB), valine (LugC) and cysteine (LugD) as the most likely activated amino acids, although with different probabilities (60% for Thr and 100% for Cys).

3. Identification of the NRPS-II Product

Figure 3A:
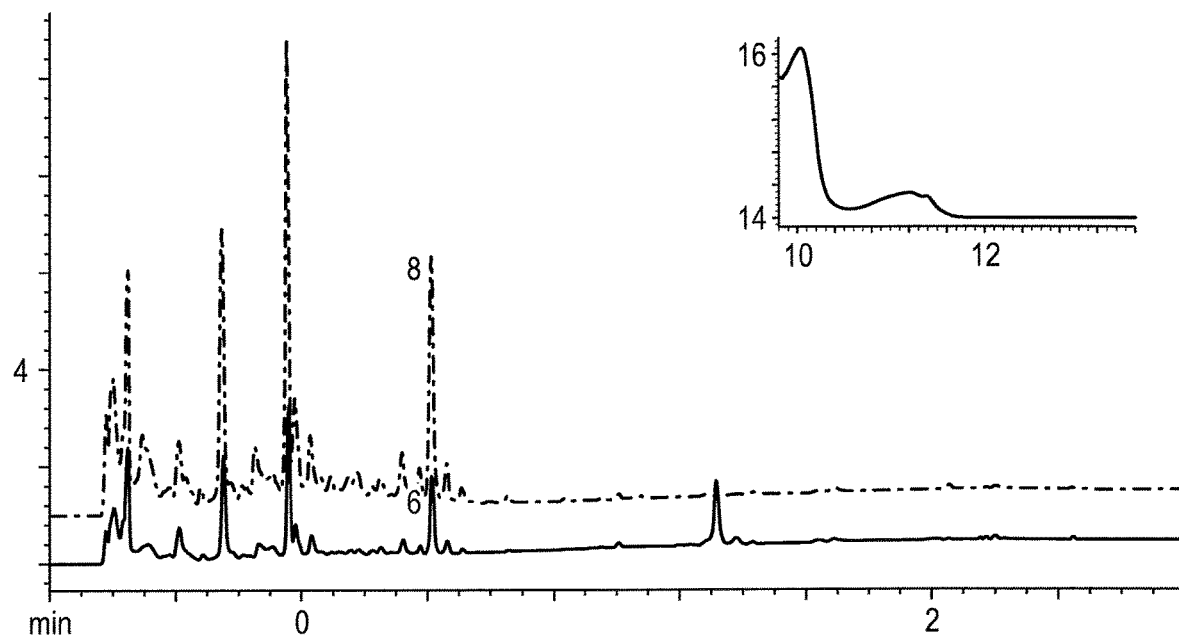
FIGS. 3A and 3B show the identification of the NRPS-II product in cell extracts of S. lugdunensis IVK28.
Figure 3B:
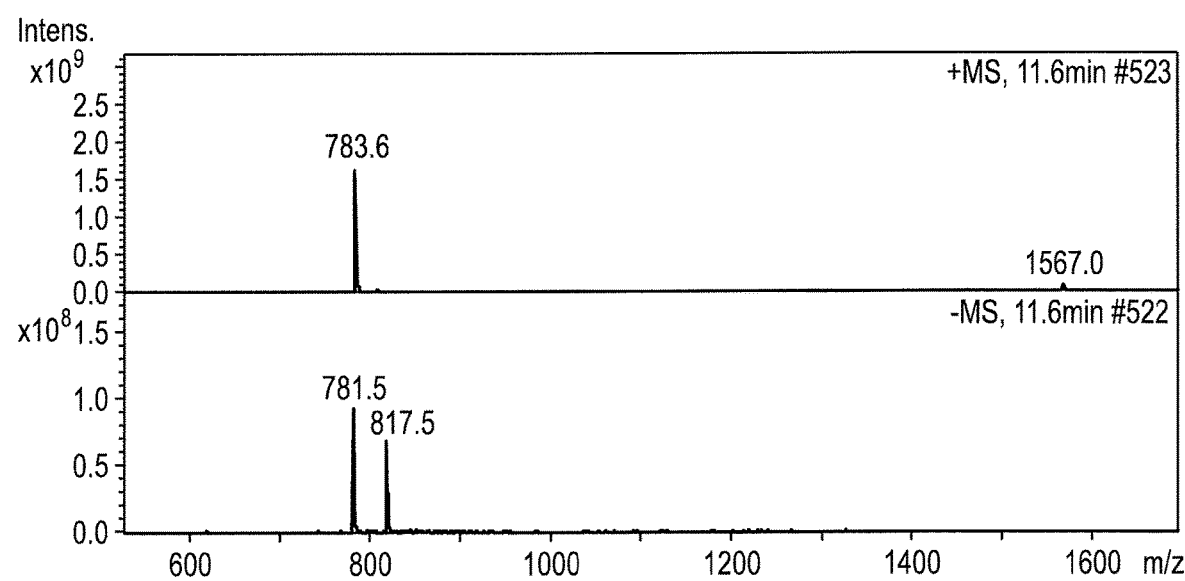

Since the inhibitory activity against *S. aureus* only was detectable on agar plates containing 200 µM 2,2'-bipyridine, the same conditions were used for an extraction attempt of the peptide. After growth for 48 hours cells of *S. lugdunensis* IVK28 were scraped off the agar and extracted with 100% ethanol. Subsequent HPLC analysis of extracts from the wild-type and the M1 mutant strain revealed differences in only one main peak at 10.6 min retention time (with a molecular mass of 782.5 Da (FIGS. 3 A and B). Surprisingly, the absorbance spectrum showed characteristics of tryptophan containing proteins at 280 nm, although no such amino acid has been predicted according to the genetic organization in silico. To confirm that the absence of the respective HPLC-peak is in fact due to the integration of the transposon in lugA and not because of an unidentified second-site mutation, a defined knock-out strain of lugD was constructed (ΔlugD::erm). As expected, the HPLC chromatogram of the respective ΔlugD-mutant was nearly identical to the one of *S. lugdunensis* M1 and did not show the peak at 10.6 min (data not shown). The production phenotype could partially be restored by complementation with the plasmid pRB474-lugD.

Figure 4A:
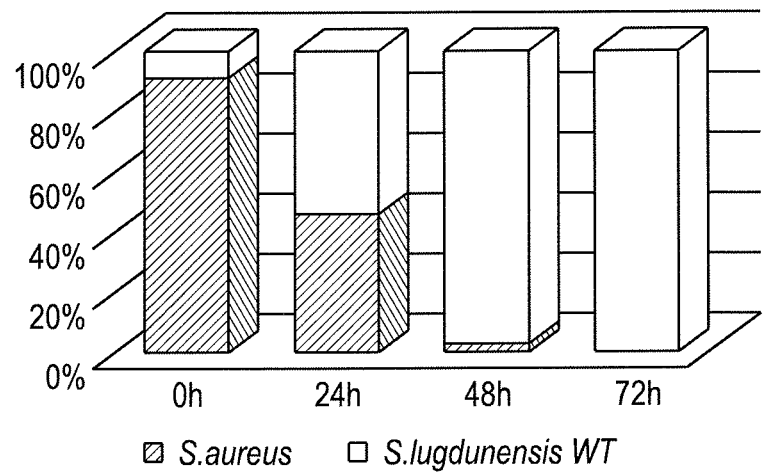
FIGS. 4A to 4C show that S. lugdunensis IVK28 is able to eliminate S. aureus USA300. S. aureus USA300 (black) and S. lugdunensis IVK28 wild type (FIG. 4A) or mutant ΔlugD (FIG. 4B and FIG. 4C) (white) were mixed in varying ratios (10:1 (FIG. 4A and FIG. 4B) or 1:10 (FIG. 4C)) and spotted on BM-agar containing 2,2'-bipyridine. After the indicated time points the ratio of the strains in the spot was determined. The figures represent the mean of three experiments.
Figure 4B:
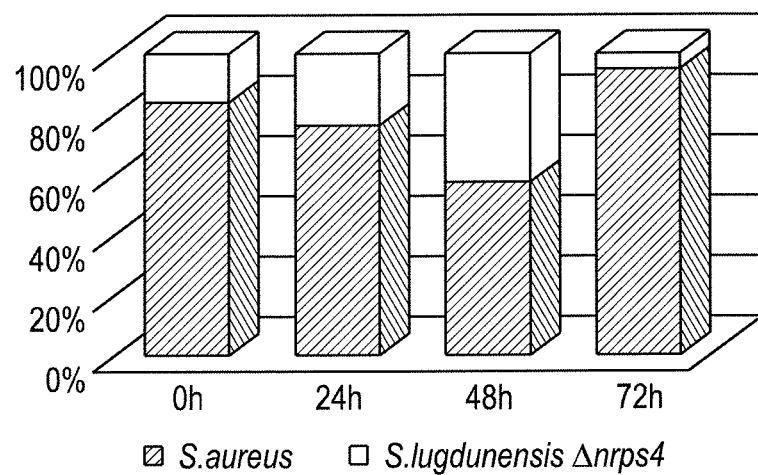
Figure 4C:
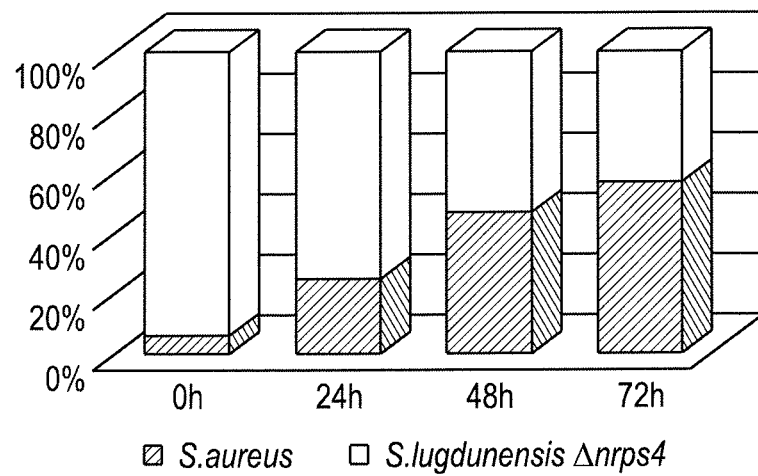

4. *S. lugdunensis* IVK28 is Able to Eliminate *S. aureus* USA300 in Co-Cultivation Experiments To investigate if the expression of the NRPS-II system gives *S. lugdunensis* a competitive advantage, strains IVK28 or ΔlugD::erm were co-cultivated in varying ratios with *S. aureus* USA300 on 2,2'-bipyridine containing agar plates. As shown in FIG. 4, *S. lugdunensis* IVK28 was able to completely eradicate *S. aureus* USA300 from the mixture within 72 hours, even with 90% *S. aureus* at the starting conditions (A). In contrast, the mutant *S. lugdunensis* ΔlugD::erm only slightly decreased the *S. aureus* ratio within the first 48 hours and was subsequently overgrown by *S. aureus* within 72 hours (B). Even more, *S. aureus* was able to displace the mutant when the starting conditions contained 90% *S. lugdunensis* (C). These results clearly demonstrate the importance of the NRPS-II system as a fitness-factor of *S. lugdunensis* in the struggle against *S. aureus*. Of note, the results were nearly identical when 2,2'-bipyridine was omitted from the medium, indicating that iron-limitation might not be the true and only inducing signal, but rather a special kind of stress like the close contact with *S. aureus*.

5. Overproduction and Purification of the NRPS-II Peptide

Figure 5A:
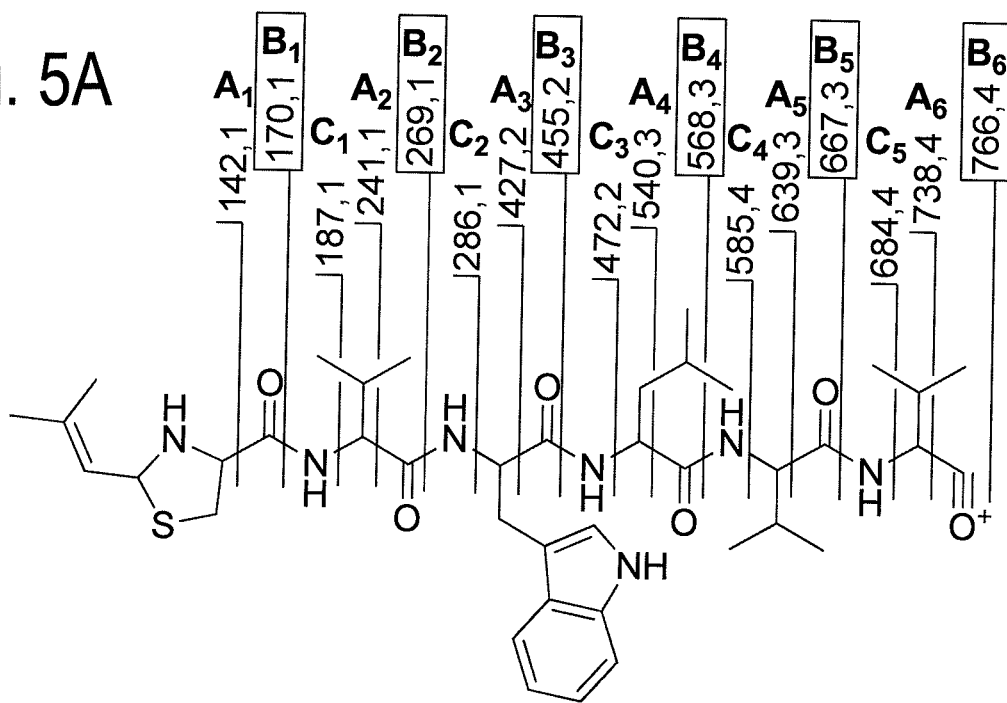
FIG. 5A shows the HPLC-MS-MS fragments and FIG. 5B shows the structural formula of the cyclic peptide embodying the compound according to the invention ("lugdunin")
Figure 5B:
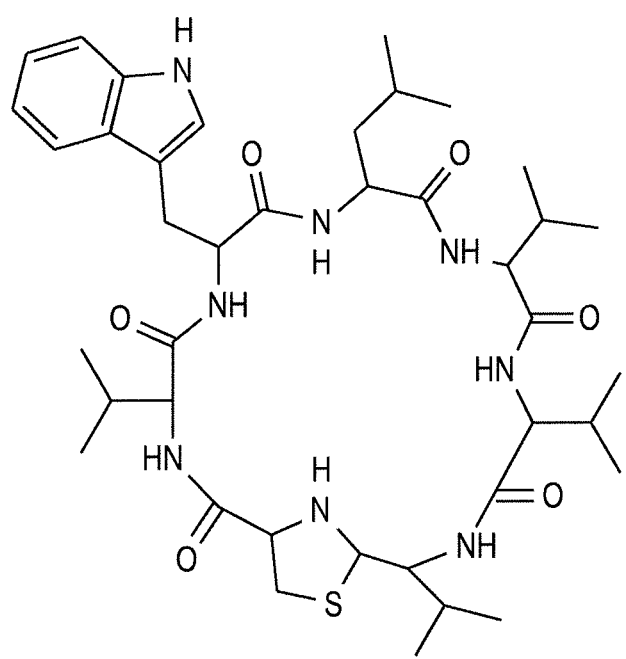

Interestingly, no antimicrobial activity could be detected, when *S. lugdunensis* IVK28 was grown in 2,2'-bipyridine containing liquid cultures, neither in cell extracts nor in the culture supernatant. For this reason the strain was genetically engineered by replacing the tetR-family like repressor gene upstream of lugA with the well-established xylose-inducible xylR-regulatory system. This enabled the inventors to induce peptide production by the addition of 0.5% xylose and in the absence of bipyridine. The corresponding strain ΔtetR::erm/xylR exhibited significant antimicrobial activity in the culture supernatant after xylose addition. By 1-butanol extraction the inventors were able to concentrate the antimicrobial activity in the solvent. After evaporation of 1-butanol, resuspension in 100% methanol and size exclusion chromatography on a Sephadex LH20 column a highly enriched active fraction could be obtained. Final purification was performed by preparative HPLC, resulting in the pure antimicrobial compound, which was solved and stored in DMSO at a concentration of 10 mg/ml at −20° C. LC-MS and MS-MS analysis confirmed the before ascertained molecular weight of 782.5 Da with the elemental formula $C_{40}H_{62}N_8O_6S$ (FIG. 5).

An embodiment of the compound according to the invention named "lugdunin" was isolated as a white solid, the UV spectrum pointed to an indole ring and HR-ESI-MS revealed an ion peak at m/z=783.4581 ($[M+H]^+$) and specific fragments in HPLC-MS-MS. Marfey's modification products of D- and L-amino acid standards and of lugdunin were also subjected to HPLC-ESI-MS and HPLC-MS-MS. Mass adducts and fragments revealed D- and L-amino acids corresponding to three valine, leucine/isoleucine, tryptophan and a novel fragment for $C_8H_{15}N_2OS$ assigned to a thiazolidine ring structure. The $^1$H-NMR spectrum showed characteristic aliphatic signals for the valine protons and characteristic signals for the tryptophan moiety. The NMR spectra pointed to at least two different isomers and conformers for lugdunin due to altered chemical shifts after 48 hours in solution. Additional 2D NMR experiments supported the structure of lugdunin. However, overlapping signals did not allow for the full determination of the regiochemistry by NMR methods nor the stereochemistry of the single amino acids of lugdunin, the order of the D- and L-valine residues is not assignable via NMR spectroscopy. Therefore, lugdunin is assigned to the cyclic peptide depicted in FIGS. 5 A and B generated from the 7 amino acids and the empirical formula $C_{40}H_{62}N_8O_6S$.

6. The New Compound is Bactericidal and Mainly Active Against Major Human Pathogens To determine the spectrum of activity, a range of clinically relevant Gram-positive and Gram-negative bacteria were used for MIC-determination. As shown in Table 1, it could be confirmed that beside various *S. aureus* strains the new compound is active against all tested species, including the glycopeptide-intermediate resistant *S. aureus* (GISA) and vancomycin resistant (VRE) *Enterococcus faecalis* and *E. faecium, Streptococcus pneumoniae* and *Listeria monocytogenes*. MICs ranging from 1.5 to 12 µg/ml (1.9 to 15 µM) underscore the strong antibacterial potential of lugdunin. Interestingly, the *S. aureus* USA300 MRSA strain was more susceptible than the laboratory strain RN4220. The producer strain showed also activity against *Propionibacterium acnes, Streptococcus pyogenes, Micrococcus luteus* and a range of other staphylococci. None of the Gram-negative bacteria was significantly inhibited in the investigated concentration range (up to 100 µg/ml).

Figure 6A:
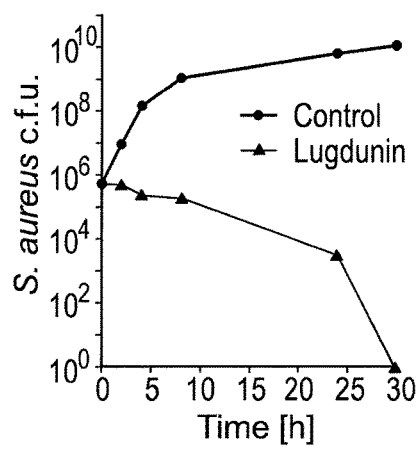
FIGS. 6A and 6B show that lugdunin has bactericidal activity and no tendency to induce spontaneous resistance.
Figure 6B:
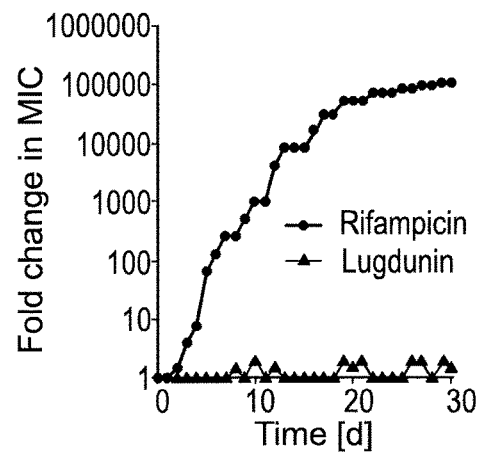

Lugdunin was bactericidal against MRSA with complete killing after a single dose treatment (FIG. 6A). No spontaneous resistance development was observed in *S. aureus* during continuous subcultivation of *S. aureus* with subinhibitory concentrations of lugdunin over 30 days (FIG. 6B). In contrast, treatment with rifampicin led to rapidly increasing spontaneous resistance within a few days (FIG. 6B).

Figure 7:
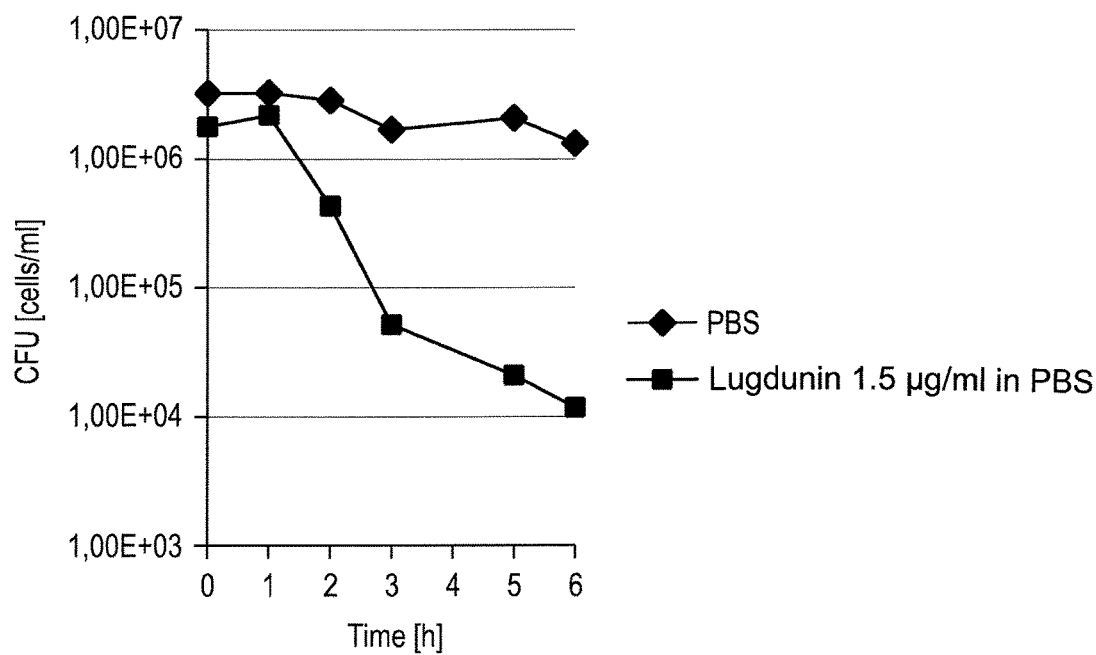
FIG. 7: shows that lugdunin exhibits bactericidal activity against non-growing S. aureus USA300. Incubation of S. aureus USA300 with 1.5 µg/ml lugdunin leads to an at least 100-fold decrease of viable cells in PBS within 6 hours.

To test whether the activity is bacteriostatic or bactericidal, killing assays were performed with *S. aureus* USA300 and peptide concentrations of 1×MIC (1.5 µg/ml). As shown in FIG. 7, a reduction of viable cells of at least two log units was achieved within 6 hours incubation in PBS, clearly indicating a bactericidal mode of action.

7. Topical Treatment with Lugdunin is Effective in an In Vivo Mouse Model

Since the effectiveness of lugdunin could be shown in vitro, the next step was the development of an in vivo model. For this purpose the so called tape stripping model was applied [Wanke et al. (2013) *Staphylococcus aureus* skin colonization is promoted by barrier disruption and leads to local inflammation. Exp Dermatol 22: 153-15]. For this model the back of C57BL/6 mice was shaved and the skin barrier was disrupted by strong tape-stripping (7 times) without creating wounds. *S. aureus* Newman (inoculum of $10^7$ cfu in 15 µl phosphate buffered saline (PBS)) was applied on the disrupted skin and covered by Finn Chambers for 20 hours to ensure efficient colonization. Due to its hydrophobic nature lugdunin was solved in 100% DMSO to a concentration of 10 mg/ml and subsequently diluted into 100% sesame oil to a final concentration of 100 µg/ml. 15 µl of this lugdunin preparation were applied to the colonized spots 18, 24, and 42 hours after the application of *S. aureus*. For the control only 1% DMSO in sesame oil was applied. Three hours after the final application mice were sacrificed and skin biopsy punches were analyzed for the presence of *S. aureus*. The inventors distinguished between the washing fraction (loosely attached bacteria removed by a washing step in PBS) and the scrape fraction (destruction of the skin material with scalpels to release bacteria from deep skin areas). FIG. 8 clearly shows the reduction of *S. aureus* by lugdunin treatment after 45 hours in the wash fraction as well as in the scrape fraction, indicating that lugdunin is also penetrating deeper tissue areas.

Figure 9:
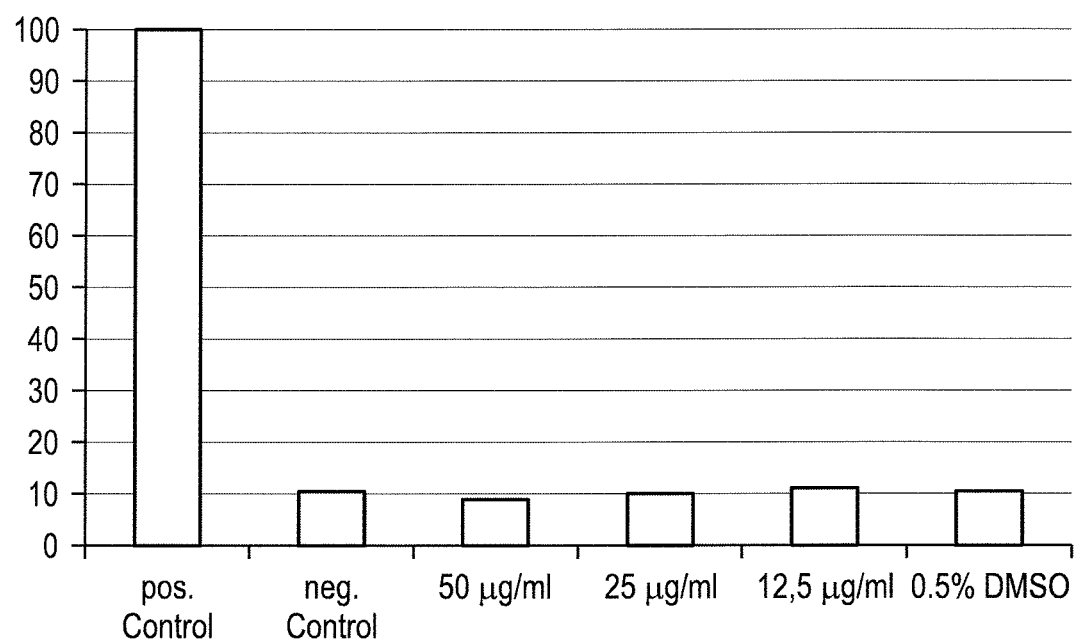
FIG. 9: shows a cytotoxicity test or the determination of potential cytotoxic effects on neutrophil granulocytes within 3 h incubation.
Figure 10A:
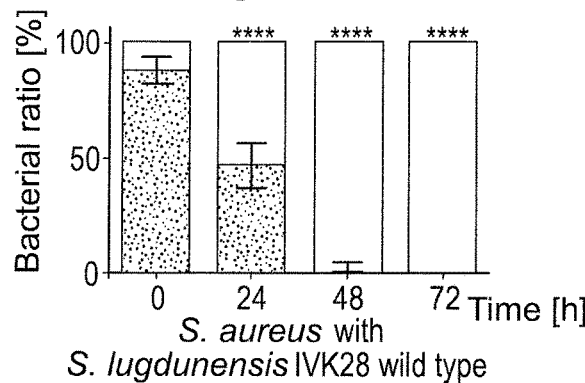
FIGS. 10A to 10E show that Lugdunin-producing S. lugdunensis eradicates S. aureus in vitro and in vivo in cotton rats.
Figure 10D:
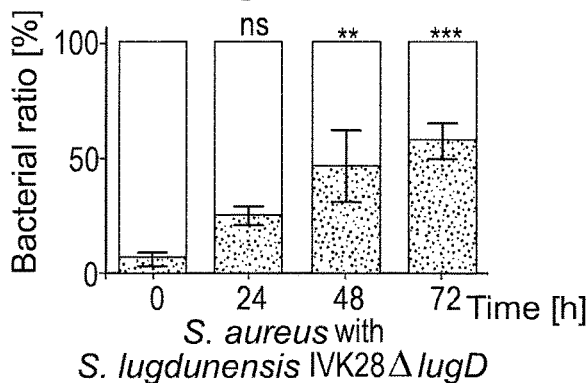
Figure 10B:
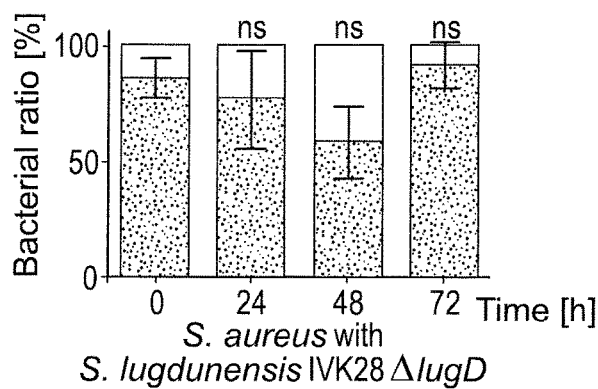
Figure 10E:
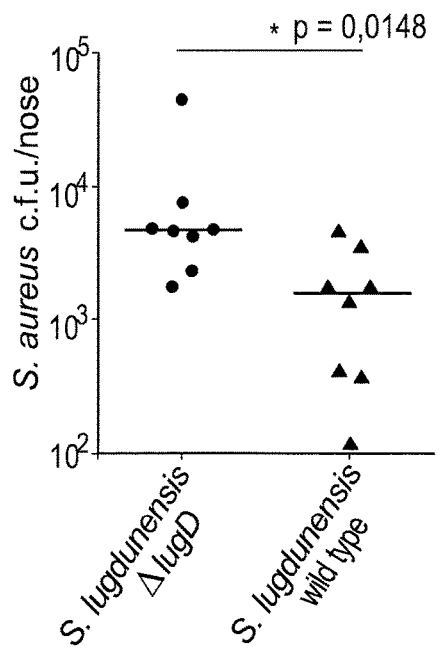
Figure 10C:
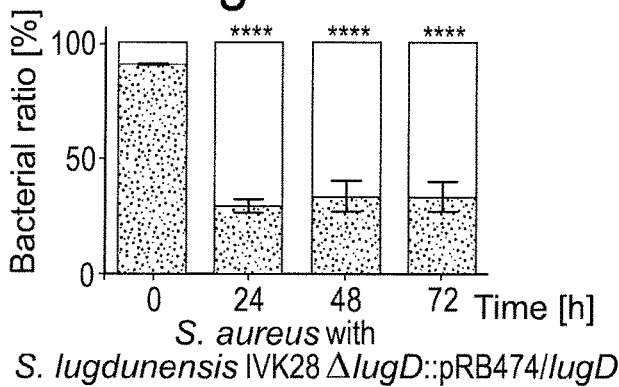

In a preliminary experiment, where the lactate-dehydrogenase release of neutrophil granulocytes was measured, no significant cytotoxicity could be observed within 3 h incubation of the cells with the peptide, even at concentrations of 50 µg/ml resembling a more than 30-fold MIC for *S. aureus* USA300; see FIG. 9.

| STRAIN | MIC | Resistance |
| --- | --- | --- |
| *Staphylococcus aureus* USA 300 (LAC) | 1, 5 µg/ml | MRSA |
| *Staphylococcus aureus* USA300 (NR5384) | 1, 5 µg/ml | MRSA |
| *Staphylococcus aureus* Mu50 | 3 µg/ml | GISA |
| *Staphylococcus aureus* SA113 | 3 µg/ml | |
| *Staphylococcus aureus* RN4220 | 3 µg/ml | |
| *Enterococcus faecalis* VRE366 | 12 µg/ml | VRE |
| *Enterococcus faecium* BK463 | 3 µg/ml | VRE |
| *Listeria monocytogenes* ATCC 19118 | 6 µg/ml | |
| *Streptococcus pneumoniae* ATCC 49619 | 1, 5 µg/ml | |
| *Pseudomonas aeruginosa* PAO1 | >50 | |
| *Escherichia coli* DH5α | >50 | |

Tab. 1:
MIC determination of lugdunin against various bacteria;
MRSA, methicillin-resistant S. aureus;
GISA, glycopeptide-resistant S. aureus;
VRE, vancomycin-resistant enterococci

8. Lugdunin Production Outcompetes S. aureus

The production of antimicrobials, mostly plasmid-encoded ribosomally synthesized bacteriocins, has been sporadically documented in individual bacterial strains from human microbiomes. However, the roles of such compounds in microbial fitness and in microbiota dynamics have remained largely unknown. To determine whether lugdunin contributes to the capacity of S. lugdunensis IVK28 to prevail in competition with S. aureus, the two species were co-cultivated on solid agar surface, promoting lugdunin production, and bacterial numbers were monitored for three days.

As shown in FIG. 10 A, the lugdunin-producing IVK28 wild type overgrew S. aureus efficiently, even when the inoculum contained 10-times higher numbers of S. aureus than S. lugdunensis cells. No viable S. aureus cells were recovered after three days indicating complete killing by S. lugdunensis. In contrast, IVK28 ΔlugD was overgrown by S. aureus even when it was inoculated at 10-times higher numbers than S. aureus (FIGS. 10 B, D). The S. aureus-eradicating capacity of ΔlugD could be largely restored by complementation with lugD on a plasmid (FIG. 10 C). These data demonstrated that S. lugdunensis can effectively eradicate S. aureus and that lugdunin production is responsible for this trait.

Figure 11A:
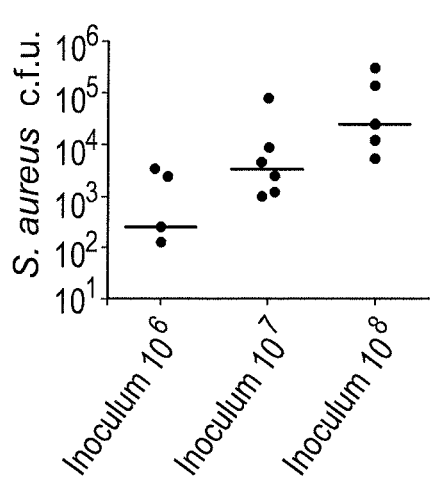
FIGS. 11A to 11C show the nasal colonization rates in cotton rats of S. aureus and S. lugdunensis. Different inocula of S. aureus Newman (FIG. 11A), S. lugdunensis IVK 28 wild type (FIG. 11B) and S. lugdunensis IVK 28 ΔlugD (FIG. 11C) were instilled intranasally to determine their colonization efficiency in cotton rats. CFUs of each strain were determined per nose after 5 days and plotted as individual dots in FIGS. 11A-11C. Lines represent the median of each group.
Figure 11B:
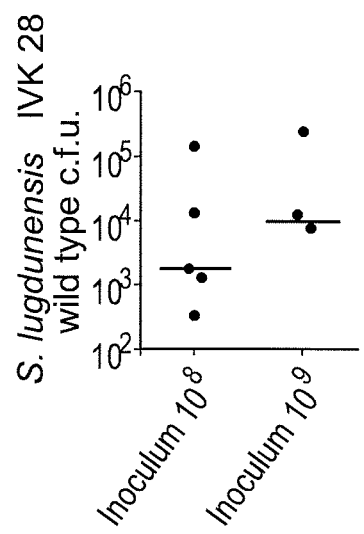
Figure 11C:
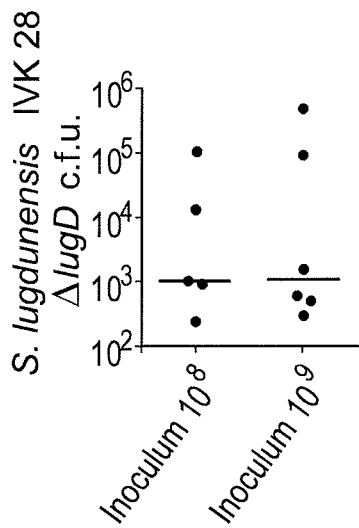

Nasal carriage is known to be a major risk factor for invasive S. aureus infections. To explore whether S. lugdunensis can interfere with nasal S. aureus colonisation in vivo in vertebrates, the noses of cotton rats, a well-established animal model for investigating S. aureus nasal colonisation, were instilled with mixtures of S. lugdunensis IVK28 wild type or ΔlugD plus S. aureus. The three test strains colonised cotton rat noses stably over the 5-day test period when instilled individually (FIG. 11). However, when the two species were co-inoculated, significantly less S. aureus cells were retrieved from animals co-colonised by IVK28 wild type compared to those co-colonised with ΔlugD (FIG. 10 E). This finding indicates that lugdunin production can effectively interfere with S. aureus colonisation in vivo.

Figure 12:
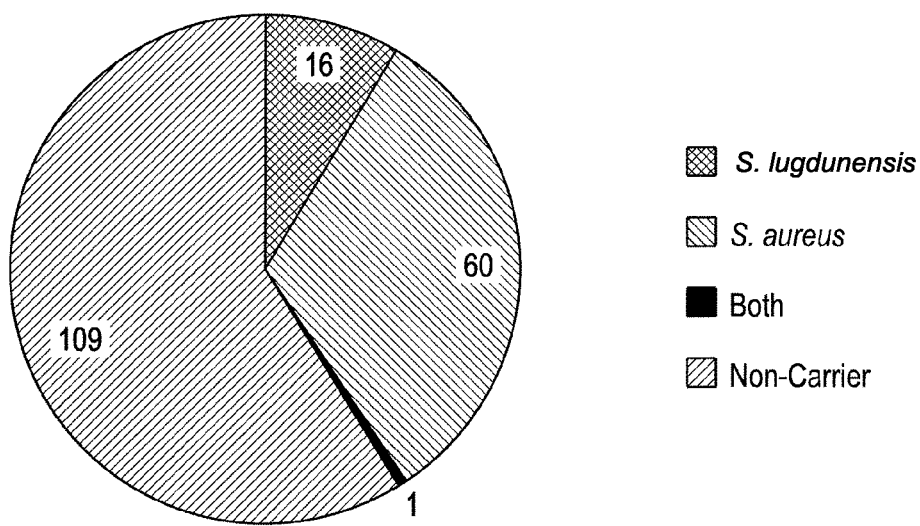
FIG. 12: shows the distribution of carriage of S. aureus, S. lugdunensis, and both in a sample of 187 risk patients.

9. The Presence of S. lugdunensis in the Human Nose is Very Likely Correlated with the Absence of S. aureus As a proof of principle of the influence of S. lugdunensis on S. aureus we investigated the co-occurrence of the two species in human noses. For this, nasal swabs of 187 risk patients were investigated. In total 61 individuals were colonized with S. aureus (32.6%) and 17 with S. lugdunensis (9.1%). None of the species was found in 109 people (58.2%). From these numbers 2.97% (nearly 6 individuals) can be expected to be co-colonized with S. aureus and S. lugdunensis. In contrast, only one person was identified being co-colonized, which is significantly less than expected (FIG. 12, $p<0.05$). This might indicate that in vivo the presence of S. lugdunensis inhibits the colonization with S. aureus by the secretion of lugdunin. In line with this assumption is the detection of the mass of lugdunin (782.4513 Da) in butanol extracted swabs of S. lugdunensis carriers, but not of non-carriers (data not shown).

10. Biological Activity of Lugdunin Derivatives

The inventors have synthesized numerous chemical derivatives of lugdunin to evaluate an abstract or general chemical formula representing the prototype of the newly found anti-bacterial activity. The chemical derivatives are shown in the subsequent tables. All synthetic derivatives were tested for biological activity against S. aureus USA300. Measured values resulting therefrom were classified and marked with "+". Derivatives marked with "+" result in the respective concentration range a complete inhibition of the bacterial growth, i.e. no growth. The categories are evident from the following Table 2.

TABLE 2

| MIC in µg/ml | | | | | |
|---|---|---|---|---|---|
| 200 | 100 | 50 | 25 | 12.5 | 1.5 |
| − | + | ++ | +++ | ++++ | |
| inactive | slightly active | active | | very active | |

Thus, the indication of a biological activity with "++++" means a MIC between 1.5 and 12.5 µg/ml. Lugdunin is the references substance with the highest biological activity and a MIC of 1.5 µg/ml. In addition to derivatives resulting in a complete killing of the USA300 test strain derivatives were synthesized which induce a significant growth reduction. They do not result in a complete killing of all bacterial cells of the test strain. Such derivatives are marked with "♦".

TABLE 3

Formula (I)

Special case for the derivative with L-Ala at position 1 (derivative 6 from Tab. 3). Here no closing of the thiozolidine ring occurs. The resulting imine (left) or the half aminale (right) howver show biological activity.

Variable cycle sizes and hetero atoms in the thiazolidin cycle.
m = 1 and 2; n = 0, 1; Y = S, O, $CH_3$ (special case upper right box)

TABLE 3-continued

| Sequence of the natural substance | | | | | | | Bioactivity against S |
|---|---|---|---|---|---|---|---|
| 1-L-Cys | 2-D-Val | 3-L-Trp | 4-D-Leu | 5-L-Val | 6-D-Val | 7-D-Val | aureus USA 300 X #1 |
| For "m" | | | | | | | |
| 1-L-Homoserine | 2-D-Val | 3-L-Trp | 4-D-Leu | 5-L-Val | 6-D-Val | 7-L-Val | ♦ |
| For "n" | | | | | | | |
| 1-L-Cys | ■ | 3-L-Trp | 4-D-Leu | 5-L-Val | 6-D-Val | 7-L-Val | ♦ |
| 1-L-Cys | ■ | 3-L-Trp | 4-D-Leu | 5-L-Leu | 6-D-Leu | 7-L-Val | + |
| For "Y" | | | | | | | |
| 1-L-Cys | 2-D-Val | 3-L-Trp | 4-D-Leu | 5-L-Val | 6-D-Val | 7-L-Val | ++++ |
| 1-L-Ser | 2-D-Val | 3-L-Trp | 4-D-Leu | 5-L-Val | 6-D-Val | 7-L-Val | ++ |
| Special case | | | | | | | |
| 1-L-Ala | 2-D-Val | 3-L-Trp | 4-D-Leu | 5-L-Val | 6-D-Val | 7-L-Val | ♦ |

TABLE 4

Formula (II)

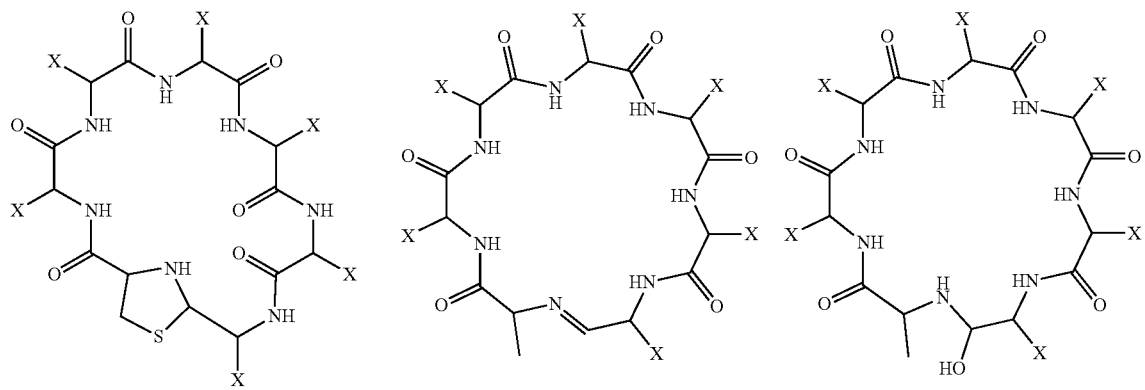

Special case for the derivative with L-Ala at position 1 (derivative 1 from Tab. 4). Here both the imine and the half aminale do prevail. A completely closed thiazolide ring does no longer exist. However, the biological activity is retained in weakened form.

| Sequence of the natural substance | | | | | | | |
|---|---|---|---|---|---|---|---|
| 1-L-Cys X #1 | 2-D-Val X #2 | 3-L-Trp X #3 | 4-D-Leu X #4 | 5-L-Val X #5 | 6-D-Val X #6 | 7-D-Val X #7 | Bioactivity against S aureus USA 300 X #1 |
| 1-L-Ala | 2-D-Val | 3-L-Trp | 4-D-Leu | 5-L-Val | 6-D-Val | 7-L-Val | + |
| 1-L-Cys | 2-D-Ala | 3-L-Trp | 4-D-Leu | 5-L-Val | 6-D-Val | 7-L-Val | +++ |
| 1-L-Cys | 2-D-Leu | 3-L-Trp | 4-D-Leu | 5-L-Val | 6-D-Val | 7-L-Val | ++++ |
| 1-L-Cys | 2-L-Val | 3-L-Trp | 4-D-Leu | 5-L-Val | 6-D-Val | 7-L-Val | ++ |
| 1-L-Cys | 2-D-Val | 3-L-Ala | 4-D-Leu | 5-L-Val | 6-D-Val | 7-L-Val | ♦ |
| 1-L-Cys | 2-D-Val | 3-L-DOPA | 4-D-Leu | 5-L-Val | 6-D-Val | 7-L-Val | ♦ |
| 1-L-Cys | 2-D-Val | 3-L-Tyr | 4-D-Leu | 5-L-Val | 6-D-Val | 7-L-Val | + |
| 1-L-Cys | 2-D-Val | 3-L-Phe | 4-D-Leu | 5-L-Val | 6-D-Val | 7-L-Val | +++ |
| 1-L-Cys | 2-D-Val | 3-L-Trp | 4-D-Ala | 5-L-Val | 6-D-Val | 7-L-Val | ♦ |
| 1-L-Cys | 2-D-Val | 3-L-Trp | 4-D-Leu | 5-L-Ala | 6-D-Val | 7-L-Val | +++ |
| 1-L-Cys | 2-D-Val | 3-L-Trp | 4-D-Leu | 5-L-Thr | 6-D-Val | 7-L-Val | ++ |
| 1-L-Cys | 2-D-Val | 3-L-Trp | 4-D-Leu | 5-L-Val | 6-D-Ala | 7-L-Val | ++ |
| 1-L-Cys | 2-D-Val | 3-L-Trp | 4-D-Leu | 5-L-Val | 6-D-Thr | 7-L-Val | + |
| 1-L-Cys | 2-D-Val | 3-L-Trp | 4-D-Leu | 5-L-Val | 6-D-Trp | 7-L-Val | ++++ |
| 1-L-Cys | 2-D-Val | 3-D-Anthranyl-Ala | 4-D-Leu | 5-L-Val | 6-D-Trp | 7-L-Val | ♦ |
| 1-L-Cys | 2-D-Val | 3-L-Ala | 4-D-Leu | 5-L-Val | 6-D-Trp | 7-L-Val | + |
| 1-L-Cys | 2-D-Val | 3-L-Val | 4-D-Val | 5-L-Leu | 6-D-Trp | 7-L-Val | ++++ |
| 1-L-Cys | 2-L-Val | 3-D-Val | 4-L-Val | 5-D-Leu | 6-L-Trp | 7-L-Val | +++ |
| 1-D-Cys | 2-L-Val | 3-D-Trp | 4-L-Leu | 5-D-Val | 6-L-Val | 7-L-Val | +++ |

TABLE 5

Formula (III)

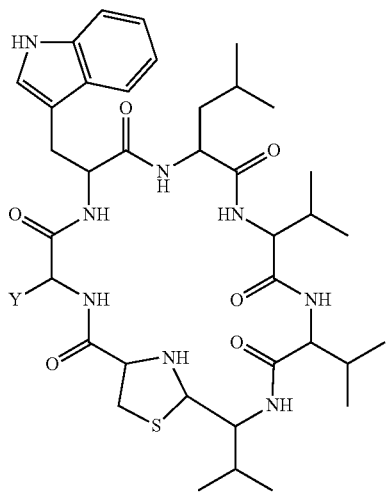

Modification: Free stereochemistry and variable position 2

Sequence of the natural substance

| 1-L-Cys | 2-D-Val Y #2 | 3-L-Trp | 4-D-Leu | 5-L-Val | 6-D-Val | 7-D-Val | Bioactivity against S aureus USA 300 X #1 |
|---|---|---|---|---|---|---|---|
| 1-L-Cys | 2-D-Leu | 3-L-Trp | 4-D-Leu | 5-L-Val | 6-D-Val | 7-L-Val | ++++ |
| 1-L-Cys | 2-D-Ala | 3-L-Trp | 4-D-Leu | 5-L-Val | 6-D-Val | 7-L-Val | +++ |
| 1-L-Cys | 2-L-Val | 3-L-Trp | 4-D-Leu | 5-L-Val | 6-D-Val | 7-L-Val | ++ |
| 1-D-Cys | 2-L-Val | 3-D-Trp | 4-L-Leu | 5-D-Val | 6-L-Val | 7-L-Val | +++ |
| 1-L-Cys | 2-L-Val | 3-D-Val | 4-L-Val | 5-D-Leu | 6-L-Trp | 7-L-Val | +++ |

TABLE 6

Formula (IV)

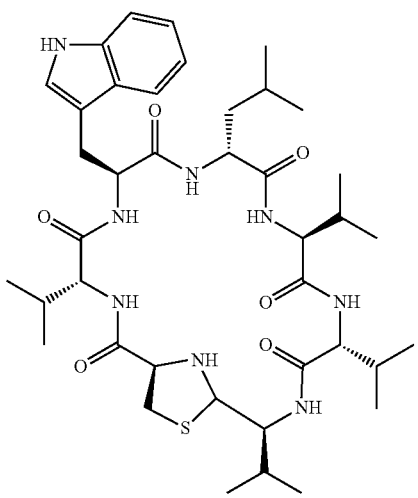 [SMILES: CC(C)C[C@H]1NC(=O)[C@H](Cc2c[nH]c3ccccc23)NC(=O)[C@@H](C(C)C)NC(=O)[C@@H]2CSC(N2)[C@H](C(C)C)NC(=O)[C@@H](C(C)C)NC(=O)[C@H](C(C)C)NC1=O]

Lugdunin naural substance as it is isolated from *S. Lugdunensis* (MIC = 1.5 μg/ml)

| 1-L-Cys | 2-D-Val | 3-L-Trp | 4-D-Leu | 5-L-Val | 6-D-Val | 7-L-Val | ++++ |
|---|---|---|---|---|---|---|---|

From theses experiments the inventors were able to identify an abstract or general chemical formula representing the prototype of the newly found anti-bacterial activity. Such formula is depicted in claim 1. The substituents m, n, X, and Y can be varied within the indicated ranges without losing the anti-bacterial activity, as it is demonstrated by these experiments.

9. Summary

Here the inventors describe the isolation and structure elucidation of the novel bactericidal peptide antibiotic lugdunin, which is active against S. aureus and other pathogenic bacterial species. On the basis of this peptide derivatives have been synthesized and tested for their anti-bacterial activity. As a result, a core structure has been developed by the inventors, which exhibits the observed activity.

The isolated naturally occurring peptide is non-ribosomally produced by a Staphylococcus lugdunensis isolate (strain IVK28) where the corresponding NRPS-operon is chromosomally encoded. However, genome database analysis and PCR-amplification experiments with 14 natural isolates indicated that the operon is present in all investigated strains, although not all of them exhibited the antibiotic activity (data not shown). Except for the description of micrococcin P1 production in the single animal associated Staphylococcus equorum strain WS2733 (Carnio et al. (2001) Pyridinyl polythiazole class peptide antibiotic micrococcin P1, secreted by foodborne Staphylococcus equorum WS2733, is biosynthesized nonribosomally. Eur J Biochem 268: 6390-6401), no NRPS-peptides are known for the genus Staphylococcus that exhibit antibacterial properties. Micrococcin P1 was originally identified in Micrococcus varians and Bacillus pumilus, but lugdunin represents the first genus-specific antibacterial NRPS product with a novel structure for Staphylococci. Since S. lugdunensis can be frequently isolated from the human nose, it is a potential competitor of S. aureus in this habitat. The inventor's co-cultivation experiments have clearly shown that the production of lugdunin equips S. lugdunensis with a strong advantage in competition. Even a minority of S. lugdunensis IVK28 cells at the starting conditions can eradicate S. aureus from the culture within 72 hours. Also, purified lugdunin is effective in eradication of S. aureus in a mouse model (tape stripping model).

Lugdunin represents a novel and rather uncommon structure since it comprises a tryptophan residue in combination with three consecutive valine residues, of which one is part of a valinoyl-thiazolidine ring structure. Tryptophan and the thiazolidine portion are flanking a fourth valine residue. A high content of alternating D- and L valine has been found in the macrolactone antibiotic valinomycin, which acts as an ionophor, but there is no structural similarity to lugdunin. A combined L-tryptophan-thiazole structure has been described for the protein synthesis inhibitors A21459 [Ferrari et al. (1996) Antibiotics A21459 A and B, new inhibitors of bacterial protein synthesis. II. Structure elucidation. J Antibiot (Tokyo) 49: 150-154], Kocurin [Martin et al. (2013) Kocurin, the true structure of PM181104, an anti-methicillin-resistant Staphylococcus aureus (MRSA) thiazolyl peptide from the marine-derived bacterium Kocuria palustris. Mar Drugs 11: 387-398], or the 7-methoxy-tryptophan containing zelkovamycin [Tabata N, Tomoda H, Zhang H, Uchida R, Omura S (1999) Zelkovamycin, a new cyclic peptide antibiotic from Streptomyces sp. K96-0670. II. Structure elucidation. J Antibiot (Tokyo) 52: 34-39]. Nevertheless, there is no additional similarity between lugdunin and the mentioned antibiotics, which makes the target prediction for lugdunin purely speculative. Since lugdunin exhibits bactericidal activity, its mode of action might differ from the other described peptides, whose activity is bacteriostatic.

Beside the use of purified peptide and derivatives thereof for eradication strategies also the preventive application of a lugdunin producer strain might be possible to e.g. clear S. aureus colonization in human noses.

Therefore, what is claimed, is:

1. A method for using a microorganism as a probiotic, the method comprising administering the microorganism to a living being, wherein said microorganism is capable of producing the compound of the formula (IV):

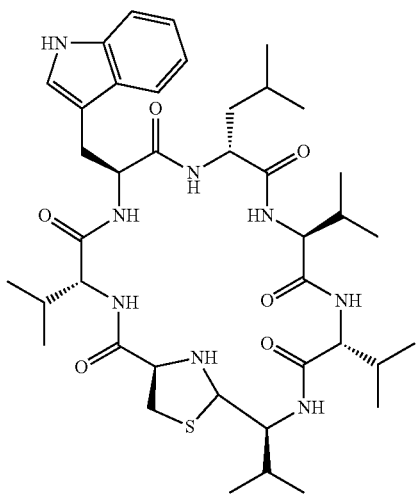

(IV)

and the salts thereof, the solvates thereof and the solvates of the salts thereof, wherein said microorganism is *Staphylococcus lugdunensis*.

2. The method of claim 1, wherein said microorganism is in a form selected from one or more members in the group of: wild type, attenuated wild type variant, modified form, and genetically modified form.

3. The method of claim 1, wherein the microorganism is administered to an organ of the living being.

4. The method of claim 3, wherein said organ of the living being is susceptible of being colonized by a pathogenic microorganism.

5. The method of claim 3, wherein the organ is selected from one or more members in the group of: the nose and the skin of the living being.

6. The method of claim 4, wherein the method is for reducing or preventing the colonization of said organ by said pathogenic microorganism.

7. The method of claim 4, wherein said pathogenic microorganism is *Staphylococcus aureus*.

8. The method of claim 1, wherein said microorganism is in a form selected from one or more members in the group of: wild type, and attenuated wild type variant.

9. A method of preventing or reducing the colonization by a pathogenic microorganism of an organ of a living being, comprising administering to the living being a probiotic comprising a microorganism capable of producing the compound of the formula (IV):

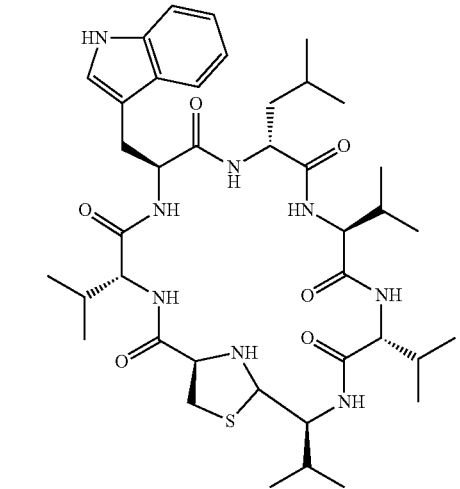

(IV)

and the salts thereof, the solvates thereof and the solvates of the salts thereof, wherein the microorganism of the probiotic is *Staphylococcus lugdunensis*.

10. The method of claim 9, wherein the pathogenic microorganism is *Staphylococcus aureus*.

11. The method of claim 9, wherein the organ is the nose or skin, and the probiotic is configured for an administration into the nose or on the skin of the living being.

12. The method of claim 11, wherein *Staphylococcus lugdunensis* is in a form selected from one or more members in the group of: wild type, attenuated wild type variant, modified form, and genetically modified form.

\* \* \* \* \*

SEQUENCE LISTING

```
<160> NUMBER OF SEQ ID NOS: 1

<210> SEQ ID NO 1
<211> LENGTH: 29605
<212> TYPE: DNA
<213> ORGANISM: Staphylococcus lugdunensis
<220> FEATURE:
<221> NAME/KEY: source
<222> LOCATION: (1)..(29605)
<223> OTHER INFORMATION: /mol_type="DNA" /note="nrp-operon IVK28"
      /organism=Staphylococcus lugdunensis
<220> FEATURE:
<221> NAME/KEY: misc_feature
<222> LOCATION: (427)..(936)
<220> FEATURE:
<221> NAME/KEY: misc_feature
<222> LOCATION: (1027)..(1266)
<223> OTHER INFORMATION: /allele="put. negative regulator of sigY (in
      Bacillus)"
<220> FEATURE:
<221> NAME/KEY: misc_feature
<222> LOCATION: (1253)..(2143)
<223> OTHER INFORMATION: /allele="ABC transporter (GdmF type multidrug
      transport system)"
<220> FEATURE:
<221> NAME/KEY: misc_feature
<222> LOCATION: (2140)..(2904)
<223> OTHER INFORMATION: /allele="ABC-2 type transport system permease
      protein"
<220> FEATURE:
<221> NAME/KEY: misc_feature
```

```
<222> LOCATION: (2917)..(3630)
<223> OTHER INFORMATION: /allele="ABC transporter"
<220> FEATURE:
<221> NAME/KEY: misc_feature
<222> LOCATION: (3623)..(5164)
<223> OTHER INFORMATION: /allele="hyp. membrane protein"
<220> FEATURE:
<221> NAME/KEY: misc_feature
<222> LOCATION: (5409)..(5981)
<223> OTHER INFORMATION: /allele="TetR/AcrR family regulator"
<220> FEATURE:
<221> NAME/KEY: misc_feature
<222> LOCATION: (6007)..(13131)
<223> OTHER INFORMATION: /allele="lugA (corresponds to SLUG_08100 of
      Staphylococcus lugdunensis N920143"
<220> FEATURE:
<221> NAME/KEY: misc_feature
<222> LOCATION: (10338)..(10347)
<223> OTHER INFORMATION: /allele="Tn917 insertion site"
<220> FEATURE:
<221> NAME/KEY: misc_feature
<222> LOCATION: (13121)..(17341)
<223> OTHER INFORMATION: /allele="lugB corresponds to the fused sequence
      of SLUG_08110 and SLUG_08120 (by insertion of one additional
      nucleotide) of Staphylococcus lugdunensis N920143"
<220> FEATURE:
<221> NAME/KEY: misc_feature
<222> LOCATION: (17359)..(26172)
<223> OTHER INFORMATION: /allele="lugC corresponds to SLUG_08130 of
      Staphylococcus lugdunensis N920143"
<220> FEATURE:
<221> NAME/KEY: misc_feature
<222> LOCATION: (26169)..(26855)
<223> OTHER INFORMATION: /allele="thioesterase family protein"
<220> FEATURE:
<221> NAME/KEY: misc_feature
<222> LOCATION: (26893)..(28632)
<223> OTHER INFORMATION: /allele="lugD corresponds to SLUG_08150 of
      Staphylococcus lugdunensis N920143"
<220> FEATURE:
<221> NAME/KEY: misc_feature
<222> LOCATION: (28640)..(29293)
<223> OTHER INFORMATION: /allele="4'-phosphopantetheinyltransferase"

<400> SEQUENCE: 1
aggtcttaaa aaagcacgtc gttctccaca attctcaaaa cgttaattgt tggaagaaat      60
atacaaaaca cctcgatatt atgtcgaggt gttttttgtg gaaaaattca gtatattgtg     120
tcttgatatt taaccaatct ttctaggatt aacttgagag gtatatataa aacatattac     180
actatactat tacgaaaaag atttctggag gaactactgt ttgacgtttt aaaactccat     240
ctaacagtct tttaaagaga gatatatgat gtgttcgtat acctattaca aaagtaggaa     300
aatcaaatta tattattaca gtcaatgtgg ccgatgttga ttttggcaat atagtcataa     360
gaaataatca tatgaaccac agtattaata gttttaactt ttgctagtaa agtgaatcaa     420
aattggttat ggaataataa caagtgaaat ggttcgctct ttgttattcg tattttgttt     480
ttcattgtaa tatttattaa ttaaacagtt aagatcggac tggaaatttt caaattcact     540
gttttctaaa tttagttttg aaatagaaaa ggtagcttta tcatccttat taattgtttt     600
atgataattt tgataagatt gtaatacata cataaaataa taagtaacaa agtctatttt     660
tttactgtaa ttcgcttgag tccactctgt ttcatcaatt ttatagcctt tagagtttat     720
tgcataatag ttttcttcac tagaacgtaa ttttttggtc tttacaattt ttaataattg     780
ttcttcaaac atagcattta catgtctata cagtgttgct tgaggcacat cttctaataa     840
ttcattgagt tgcataatag aaagtccttc tggtttatcg attaatgtta atgcgatttt     900
aaaacgtgtt tgatttttaa ataaactgaa ttccatacat aacacctcac tttatacata     960
ataattgatt tttaaataaa tgtacagtaa cattatcatt atcaataatg ataatggagg    1020
```

```
gtgaaaatga atactgatat taacgtctta aagaaatag  actgggggac tattatgcca   1080
atattaatac caatattggt tttacatgta gtacttttaa taattgccct aatcgattta   1140
tatagacgaa gaaaaattgt taattatcct attgcttggg caatcgcaat tttgttgttt   1200
aatactattg gacctattct ttatttgatt attggaagga ggctaataaa aattgatcga   1260
gattaagcat gtgaataaaa tgtttagagg aagaaaaata ctgaaaaata tttctttttaa  1320 tatttcagag ggagagtgta ttggattatt aggtcctaat ggtgctggga aaacaacatt   1380
gattaaatgt attactggaa ttattaatta tgaaaaggg  gaaattaaat ttaatggaaa   1440
aaatattttg aattttaaaa atgatattgg ttatttatca cagcacacag attttaagca   1500
gtggatgact tgtgaagagt cgttaagatt ttttggtggt ttatcaggtt taaataaaac   1560
gtatattgct cagaatatta ataaaatact aaaagatgta ggtcttcaga ataaaaataa   1620
atataaggta gaagaattat caggagggat gaaacagaga ttaggcatag cacaggctat   1680
tttacatcgt ccaaagtttt tggtcttaga tgaaccagta tcagctcttg atccagttgg   1740
caggaatgaa atcaaaaacc taataaaaaa attgaaaaaa tacacaacag ttcttatatc   1800
cacacatatt cttgatgatg caagtgaatt ttgtgatcga tatattatta taaaagatgg   1860
agaaatcatc ggaaatataa ccaatgaaga tgagactgtg aattacaaaa gtatatattt   1920 aaaaattct ttaaaagatt cttatgatcc ggatattcaa ttaaccgact tatatgattt    1980
acaaaaagta aaagcaggag aatatattgt aaccagtcga aagccaattg aaatatctga   2040
gttaattgaa gaactggaca aaattaatat taaagtgaat tcaattgcat atgaaaagaa   2100
agatttagag aaaaatattt tagagttggt gtctgatata tgagaaatat attaatttta   2160
ggaaaagtgg aattattaga agcagtaagg aacattaaat ttatatggtt agcaatattc   2220
ttttctattc ttggattgac gcaacccttta attgataatt acatggaagt gattattaaa   2280
aattttggag gggttgatgg gattattatg gaccctaatg cacctaaacc tcaggctaat   2340
gaagttttgt tggcaacgtt tactggccaa tttaatcaga tgggtttgat tgtattggtc   2400
atcagcttta tgggtatgat agctgatgaa aagaagagtg gagttctggg gtttatattt   2460
acaaggccag tatctagtat acaatatatt atttcaaagc ttttttggaaa ctggattatt   2520 agtatgatat gtatcttgat tggtgctggt gtttcatatt gttatactat ttatcttttt   2580
gattattatc catttattaa ttttttattt tttctcttat tttatagttt gtggattctt   2640
tttattgtca gcgtaacgat attattaagt acttttataa aaagctctat ttttataggt   2700
gtgataacta tcgtaatatc aatggtattt atattattgg gcaatattaa taaacatttt   2760
gctttatttt taccaagtgg tgcacttaca ttagctgaaa gccaatttca aaatataaat   2820
tctaatttct tattgataat cgcacctgtt atttatattt ttgccttagt atatgcatct   2880
aaagtcatta tcaagaaatt ctaaggaggt atagaaatgt tatccattca aaatttaagt   2940
aaaacgtata aaggttctga taaggtgtt  aagaatttat cattagaatt atatgaaggt   3000
gatatatgtg cttttattgg agcaaatggt gctgggaaaa cgacaacgat taaatcaatt   3060
gttggaatac atacatttga tcatggagaa gtgaaattgt tcaatataaa tctaaaagat   3120
aatccagagt attataaatc tttcattggt tattcaccag atacgcctga tttgtacaat   3180
aatatgacgg ggaaagcata tattgaacta atagcggcgc tttataaaat ggagaacata   3240
gaacttgaag agaaattaag ttacctaata aaagaattaa aatttgaaag tgccatttat   3300
gatttggttt ctagttattc tcatggaatg aagcagaggt tagtgcttat ttcattatta   3360
```

```
atgcatgatc ctaaattaat tattttggat gaaccatttg ttggcttgga tccaaatgct    3420
attgattttt tagtgaatga aattagaaga cgagccagtg aaggagcaat tattttatac    3480
tctacacacg tacttgaagt tgctgaaaaa ttatgtaata aacttgttat tttagatcat    3540
ggtaaagctg tagtaaatga tacaatggaa agtattctta aaaaagcacc attaaatgaa    3600
atatttaagg atgtgacttc tgatgaataa tcttaaattg ttatttttat ttcgattaaa    3660
aaatcaaacg caattatcta atttgaaaag caataataaa gaagtaagaa agcattctat    3720
ttacactatc acaggatata ttactgcatt tataatgttt ttaggatata tagttttcat    3780
tgcaatagat ttaagtttaa ataataatat ccatgaattt tttgtattat aacatccat     3840 tttattttgg ctatttggta tatggaatat acttagcgga ttcgataatg tcatagaagg    3900
gaaggatggt gaattatttt atagtctgcc aataaaaaac tggcaagcaa aactgtttta    3960
tttattaagt aaatatttga ttcatattac tttgactttt accatttta ttctaagtgt     4020 tgtcttcgta atacctttgt tatctcattt attgtcagta attcttatga ttattttatt    4080
aagttttatt gttcctcttc tagctacaaa tatacctttt ataatttcca tattagtaag    4140
aaatatacta atatttatca agttacgtaa taatataaca gagtcaattt ttacattatt    4200
cgcatttata gctccgttaa tttatttat ctttaactct gaaatggttg gttataaaga     4260
atggtttata aatacatcta ttttacggta cccgcttaac aagatgacta gctctccttt    4320
tttatttaat atgttttgt taattgttat taccttatt acaacgttca tagttatta      4380 tatgctgatt aattttcatg attcccttag aaatcaaaca aataagcgaa agaaaaaaag    4440
aaatgggaat acgtattta aaataaattc accagtattc agtttaataa taaggaatt      4500 taaattatat ttttcctctt taacttatgt tagtaataca atcataactc cagtagttat    4560
tgttatacta aatataagta ttctaattgg aataataccc agtattgatt caatttctta    4620
tgatttacta ggatttacta ttagttctca gcaaatatat gtacttattg tctttacttt    4680
tgtaattctt actactacaa cttccttgtag cattcttttt gaaggaaaga gtatttggat   4740
tatgttagtg gctcctatta atattaagaa aatagcgatt ggaaaaatat tagttaatat    4800
acttttattt ttaccaggta ttgttttaac ttcattgtg ttctatacag tatttcatgc     4860
aggtatattt tatttaatta taatcagtac gttgttagta tctaccctca ctttgataag    4920
tattattggg ttttagtaa atttacggtt cccatcctat aactggagtt ctgaaatgga     4980
agttgttaaa caaagtaaag gaactattgt aactgcaata ataagtatga taattattcc    5040
gatagttatt gcatttgttc taataaataa ctcattgctg actttattgg taattttat     5100 agaaatggca gtgattataa ttatgtttaa aaaaattaca gcagatagtt taattttaaa    5160
ataataaagt atgtaataag aaatacaatg taaatgtagt ataaaatccg caatagaata    5220
ttcttattat tagaagatta gttgacaaaa tattttattc tttatcttta gagatgtaat    5280
agacacaata aagaaaaatc aatatttaaa aaaatattcg cttaatatag ttgacatatt    5340
aattaaatag attaagataa aagtgactag aaaaatttat ttagtcataa atgaataggg    5400
gtattaatat ggcattctct aagattgaaa aagaaatat taagaaaaat ttattagaaa     5460
attgtgaaaa gcattggtca aaatacggtt ataaaaaaac aaatattaat gacttgtgcc    5520
aaatttctgg aatatcaaaa ggttcttttt ataatttttt tgattcgaag gaggcattat    5580
tttatgaagt catcataagt gcacacaata agttagtgaa aattacagag gacggtttaa    5640
aaaaatgtat gactaaatat gatttgcta attttttgaa actgttatat caggaatata    5700
caaaattaga ttttttaaat gagacatcac aacaggattt tatcaaattt ttaaataaac    5760
```

```
tagatgtaaa aaaacaaaaa aaattaatgg aaaatgtaca ctatgatctt cgtaatgaaa    5820
ttaggaaatc aaatttgaaa tataaagttg atgaaaattt agggatttct gccttaggat    5880
atatctttac tcctttatca aaagaagagt tagatatata taatgaaaat ggaacaatcg    5940
agtttttaat tgacataacc gttgatagga tttttgaata agttttagtt aaaggaggtc    6000
aatcagatgg aattaattaa atcatcctat atgacacaag cttctatgga agaagaacaa    6060
ctttatttga tatggaataa atcatctgtg actagatcgt tatatacgga aacatggtgt    6120
tttaaattac taattgaatg tgacaaaaat aaacttgtga agcactttg tcaaatttt     6180 gaagaaaatg atattctaaa atcaaatttc atatttaaaa ataatcgtgt ataaaatac    6240 gtaaatcata cgaatcctgt tgtgataact gaaaagtga aagagacaaa tttatatcag    6300
tttataaata aatacaaaac ggaagagttt gatttaaata atgacgtcct atgtcagttt    6360
tatattttaa tagataatga atgaatagc acttatctta ttataaacca ccaccacatt    6420
gtatcagatg ctcaaacaaa aaatttaata cttcgaaggt taaaagagat actagatcca    6480
agtagggtta ctgaaaaaat tcatcatgaa ttatctacta attatcaaga acacttaaag    6540
ccattaaaaa agctcaaaca agataaatac atacaaaaag cacttgatat acctcgtcgt    6600
attaagcctc atagaatttc acaaactaaa tttactggct atactaagaa tttaaaacta    6660
aataatgaaa agttccaaga attagtaaca tattgtaaca taaataaaat ttcaaaatac    6720 acttttttc taactacttt ttattacact ttacttcata ttaccggtga ggattatttc    6780
agattaggta tacctttctc tactcgaaat aatagtgagg attttaaaaa aatgggatat    6840
tttgtgaata tattgccttt atatattcag gatagtattt atgataaagg ttatacctgg    6900
ttagataggt ttaaacttgt tcaaaaagaa atatttaaaa catttgaata taagaatgca    6960
cgttatcggg atttaactac attctttgat tcgccattaa acagaatgca agatgtagtt    7020
tttagctacc aagaaacaga taagaatgtt tcggacattt tttatgagat taatacaaat    7080
caaacaggag caaagtttga attgactggc aacgttaaag ttttaggaaa tgaagcgttt    7140
ttggaaatcg agttctctga tgaaatattt aatgaagaag aatcgaaatt tttgattgat    7200
acttataaaa gtataattga taaagcttta aaaggtaatg attttgaaaa tagaggaagt    7260
aatgatagct taattcaagg taaaaaagtt agtctagaaa aaaataataa tcttatataa    7320
gaatttagaa atatagcatt taacgaaaaa tataagcaca aaatagcaat tatgtcaaaa    7380
caatatcaaa ttacttattt cgaattaaat acattggtcg ataaactagt aaatgcaatg    7440
ttaaattata aaatttctca ggatgacagg atagctattt ttttagatag aggaattaag    7500
aatattgcat taatgatagc tttagctaaa atgaatattc cttttttaca tttaaataat    7560
aactatcctg aagaaagaat taaatatatc ttagatgatt ttaatgcaaa atatgttatt    7620
acagataatg caaatcattt aaaaataagt gagaaacaaa aagttttaga tagaaattta    7680
ttcatttatg ataatttgaa ttacaataaa actcttgtt ttagggaaga tgaaaactgt     7740
ctggaggtat tttatacatc tggtacaact ggttttccta aaggtgttaa aataactcat    7800
aaaaatgttt tcaattttac ccggaatttt gaagcatatg gtttaaatga taaggatgtc    7860
tttactcact gcagttcttt atcatttgat gcttctacat ttgaaatatg gatgtcttta    7920
cttaatggat gtagtttatt agtggttccc gatccaataa ttgatattga aaattggaat    7980
tttgaggaat tacaattaaa acctactatt tctttttttaa caacatcgtt gttttattct    8040
atgattgata atgagtcaat acaattgttc aaagatcata ggaaaatttt tattggtgga    8100
```

```
gaaaaagctt tagcaaaaca tattaaaaaa gcaattaaaa acttagagaa tgttagtatt    8160
gttaatggtt atggtccaac tgaaaatact acttttacga ctacaatgga atttaataat    8220
tcattctttt ctaacgttcc tattggaaaa cctggagtca atgtgaaaat cggcgttgta    8280
aataaaagaa atatgcttct accacataat tgcgaaggcg aaatagtaat tggtggtgaa    8340
aatcttagtt caggatactt aaatgaaaat attacaaaag aaaaatttgt gacgattgat    8400
gaagtgactg acaagttata taaaagtggt gatattggtt atatttcaag tgattcaacg    8460
cttaattata ttagcagaat agatagccaa attaaactga gaggatacag aatagagtta    8520
tctgagattg aagaaaatct acttaagcat gatttagtgt caaattgtgt tactgaagtt    8580
atcaataatt tattagtatt agtttatgaa ggtcaactaa agactaataa ggctaaagag    8640
tttttaacta atgtattgcc aaattatatg gtgccaaatc aaattattca taccgataag    8700
attccattaa cgttaaatgg caaattagat aaatcaatta tagaaaagtt ttatatagaa    8760
aacagtgata atattccggc cactaaagaa gaaaaaatga ttatggaagt aataaaaagat   8820 gccacgcata gtcaaagtgt tagtacgaaa actaatttat atgaaattgg tatagactcc    8880
attaaatcga tgcaaatttg ttctaaatta agaaataaag gttataacat tactatgagc    8940
gaatttatgg actgccaaaa tattaaaagt ttaggagaat ttttaaaaa agaaaataat     9000 aaagaggtac gccaaaataa tcagatttgg aattcaaatg aacttagtcc aattcagaaa    9060
tggttttttg aaacacagaa agaagacata tctcattgga atcaaagtgc tttaattgaa    9120
ttaaaaaaca taaagaaga aaaggatatt attaattgct aaaacaact tatcgaatta      9180 caccctatat tgaaatcacg atttatttta gataacggtg tctataggca agtcatagat    9240 aaagaaaat atgagataaa ttcagagaaa gtacagagtt taagtgaatt taataactta    9300
ttaaatattg ggcaatcatc actaaatatt cacaaaggta tatacaattt taaaataata    9360
tattatcaaa atcaagtata tattcacttt attatacatc atttagtgat tgacggggta    9420
tcatggagaa ttattttaaa tgatttctct gaattattag aaggtaataa taagtataat    9480
tatgaatcga gtaactttga tagttgggta aaatatataa aaaattatga agatgggcta    9540
tcagaaaatt attttttcgga atggaagaat cagattaata ataacaaaaa gtgtaaaatat   9600 aaagatttaa aagattatga catagcattg agtaaagagg aaactgaagt tataattcga    9660
ttcgcgaatc agaagaacca tggaaacatg gaggctgttc ttattgcagt tattgcacat    9720
actctaagta aaaataatat catacccccaa aaatctattt tactattaga aggccatggt    9780
agaccaaaag aaaagaatga gtttattaat acaatgggct ggttcacaaa tatatatcca    9840
atgaagatag aactaaatga tgatattaaa atatcagctc aaaagatctt ttttaatcaa    9900
ataaaaatcc ctaataaagg aatcggctat caaagatatt ttgatttgaa tttttgtcat    9960
gattggagtt ttaacttttt gggtgatatg acatttaatg actatcctga gtttaagata   10020
gtagatattt tttcagaaaa tgacttttct ccaaacagtc aggctttatc aaatctgcat   10080
gtagatgtta ttttaaataa tcaagaatta agtattaaat ttaaatataa taaaaaacta   10140
tataatagtt cggattttaa aaaagtggaa atggaatttc aagattcact atatttgttg   10200
aaagatgctc aaaatggtca aatatatcca attaatcgaa ctcaagaagc aatgataatg   10260
gattattatc aaaatcccaa aagtggaaat tacattattc aatgggaatc tgaaaccaaa   10320
aacttggaag tagaaaaaat cttaagtgca attagagaat tgcttcgaaa agtagaacct   10380
ttaagggtgt ctttttctga gatagatgga gaatggtatc agaaggttaa tgaacttgat   10440
gattttggat taaatcagct tataaaaatt tttgacttta gtaacaatag caactcaaat   10500
```

```
aatcttataa ataatctgct tataagtcaa agacacatac cgtttgatat tcagagagga   10560
ccattaataa ggtttcttat tgttaaactt gaaaatggtt ataaaataat tatggaaaat   10620
catcatttaa ttattgatgg ttggagtatg tcaacaatct ttaattattt caataaatta   10680
tatgataatg ataaaaaact cagagatatt aacattcttc aggatagatt aattagtaat   10740
actaagccaa aaaatctaga tgagtttaaa gatattttg aaaaatatga acctattaac    10800
ttacctaaga tttctaatga aggtttagag gaagaaacaa tctatataga aaaagtgat    10860 aaacattata gttttttaga aagtaacagt ttaacaccaa ataattattt tctattactc   10920
tggtctctga cattgaaata tttatttggt aagaacgata tcttgtttgg agtgacaaca   10980
tctggtagaa gtaaatttca tagtaatgag atagatggag ttggtatgtt tgtaaccact   11040
ctaccattca gaattgattt tagagattgc caaacaataa aagaagattt aattccaata   11100
attaaagata aaatgaattc tattttagaa aatgatttta ttacatggaa agatataata   11160
atggaatcaa atatagataa tgaaattcag attggttatg tatttgaaaa ctatcccaaa   11220
gtacaaacaa atggaatttt ttcatttgat acttcaaaag gacatgaaca ggttaatttt   11280
ttgttggcat tatctgtgat tgatatgaaa cataattata aaatagatat aaaattagat   11340
gagaagtttg ttaataaaga catgttgcat agctgtaaaa tattgcttaa acaaattaat   11400 ctgttttag aaaatcagat taatgaagtg agtgaaattt caaataaatt acttagcaat    11460
acttcacttt atccgcaagt aagggttatt acggaaatta atgagactgt ttcgagtgta   11520
ttaatacaac agttttttaaa atataataat aaattgttga taaaaagcaa agaaaaagaa   11580
tacacctata atgatgtata caatattgtt cgaaatatta ttaatcgtac tgaactatca   11640
gatagtgatg tagttgcggt gatgacaaaa gatagaacaa aaatgacttt atatgcaatt   11700
gcatgtttca tatccggagc aacttatata cctataacag aggaaattaa taaaaataga   11760
attgaaatga tgattaataa tgccggagta aattgtttgt ttaatggcga tggttccttt   11820
agtcgattgg aaggtacttc aacaacttca cttgatgata tagcttatat catttataca   11880
tcaggatcgt ctgggtacc aaaaggagta aaagtttcaa agtataatct tactaacctc    11940
ttaaaagcat tggctaggga acatatagct aacgagtcag atatttggta tcaaaatata   12000
gtgatgaatt ttgatccatc catattcgat cttctaatgc ctattattag tggatgttct   12060
atgtatattc ctgagaaaag attatacgct actgaaatcg aatatttgct cgaaaaagag   12120
aaaattacaa ttttttcgat gactccttcg cttgctaaaa atttagaact gaaaaataat   12180
agcagtttga gggtaatgat tataggtgga gaaaaattaa ctaaaaatga tattgaaaat   12240
ttacccaaaa aaatagaaat aattaatatg tatggtccaa cggagtcaac tattatttcg   12300
aatatgtttc gaataaacag cgaaaatata atgattatc tccattatcc aataggcaaa    12360
cctataagta gtttgaatgg ctttacaata tcacccgata aacaaatact gccgtttgga   12420
gttgtaggag aatatgtgtt aaaaggttct acagttactc aagggtatac agataaacat   12480
ttaaatagta attttctgat tgaaaataac aggaaaaatc attttaatac aaaagacctt   12540
gtttatattc aatcaaatta tctaacccat tatattaatc ggttagataa tcaaattaaa   12600
cttaggggtt atagaattga gctaggagat atagaatcag cgttaaataa gataatgcct   12660
agtaactcct ataaattgat ttttagtaat aataaggatt taatttttagc ttatactgcg   12720 aactacaatg aggaagaaat acacgtattt ttgaagagaa atttacctag ttatgccgtt   12780
cctaatttca tcaaatatat cgaagatttt ccgataacaa ttaatgggaa aatagatttc   12840
```

```
aaagaaattg aaagtatagt aaaaagagag ttgaatttta atatcgatat caatcaatat   12900
aatgacgata ttttagaatt tttaacacta tgctctgata cattggaaat agggaaaatc   12960
gatttaaatg ataatttctt cagtgttgga ggtgattcaa ttaaaggtat gaagctgatt   13020
agagcattaa atagggaata tggagttgaa atgaaaataa aggaattgtt taaagccagt   13080
aactttagcg aaatttattt actattaagg agggataaaa gtggtaaata aactttatga   13140
attgagtcca cagcagaaag gtatttggtc aagaatccaa caatatagag aaaataatga   13200
atacctaatt cctttagtca ttcaacttga tgaaggtata aaaaagaag atgttgaatc    13260 agcacttaat gaaattatta aaagtaattc tgctttaagg gtagaaataa tgatggggaa   13320
attcccgaaa caattgattc atgaaaaagt aaatattgaa ttaagaaata taaatttaat   13380
agataatgaa aatgattttg aatatcaaat aaaaaaatat atcgaagaac caatgtctct   13440
ataccaaaaa ttatgcgatt ttaaattatt tcaacataag aaaaaaaact ttctagtttg   13500
taaattccat cacattattt tcgatggtca ttcaggaaaa atatttaaag aagaattaga   13560
aaggcaactg tctttaaaa aaaatatatg tataaaaaat aacacttttt atgagagcta    13620
tttaaataaa gcatgtgatc aaattgtttt ggaggaagat aaaaaatatt ggaacaagat   13680
ttttaatagt gagattgatg attatttcat gattaataat aaagaaggaa acgaaaggat   13740
tgaatatgag aatgaactaa gtgtaagttt aaataattta aaagagcatt cacatcaact   13800
aaaacaaagt ttatttttcaa cactcttagg tttatttcgt ctctatgcat ctaaacattt   13860
taataaagaa acattgtcta tcgcaatacc tgtctcttct agacgttcgg aacaagatta   13920
taaaactata gggtacatta cgcaggtatt tccccatgta atgaaggtgg agaaacagaa   13980
aaattatgaa gatttacaag aatattctaa tcaattgctt tatgaacttt tagagcattc   14040
tgatctttca attattgaat tatctaattt aagcaaaagt gcttccaaga atattgagga   14100
ctattataaa tgtatatttg atattgtcga agaagaatcc tatttagata ataaagtaag   14160
aatgtggaat ttacaatcag agtacccatg gatagttaaa gttatcatta gagatcagca   14220
agtgtttttg aattccaatt ttaaaaaaga acttttccca ttttggaaga ttagggattt   14280
tcatgaagga tttaacttct ttattaacaa tattattagt gaatctggaa gttatttta    14340 aaaaaatgtt ggtatgccaa taaagaatt aaataaaatt ataaatataa gtaactttgc    14400
agcttctaaa aaagacatta attataataa atcgaaatta gacgtaaaaa ccttaatgta   14460
taatacggcg ataataagtg gaagcgaaaa aatttcttat aaacaattag aagaagattc   14520
aatcaaattt tctggattta ttaggaatag gaatttgaaa gtgggggcaa aatgcctcgt   14580
ttatatgaat gatactcttg aagctgttag aattttctat tgcttacaga aaacaattg    14640 ttgttttata ccggtttcta atgacacacc tttaaataga gttaagctta taattgaaga   14700
atcaaacccg ctccttatt tttcagacat tttagatgga agtgaaacag ataaaatatt    14760
agtgagtaaa ttaaataaat gtcattgttt gagcccaaac acaataatta gaggtactga   14820
tgagaactat tcacctggca catccatatat tatatttact tctggatcaa ctgataagcc   14880
gaaaggtgta atgattactt ataagaattt gtctggatta attactcaat acaaaagttt   14940
atttgatatt caaaaaggag atagagttgc tcaaatagcc agtttgaatt ttgatgctag   15000
tatatttgaa atgacattag ccttttcaac attttctgta ttgattatct ttaacaataa   15060
tggaggttat gagaacttca atcagtttat tatagataat agtattaccc atttttttaat   15120 gacacctgat tattatgctc tactagactt tagtaaatgt aattcattaa aaaatataat   15180
tgttggtgga gatgaattta agtttaatga tactgtacct gaaaatgtta agatatttaa   15240
```

```
tgcctatgga ccaactgaat caacagttat gtgtttaata agttaatga caaaaaaagt   15300 aaaaacctca aacttaggta aaccaatatt aaactcagga gttattttat taaacaataa   15360
tggagagata ataaatcgtc atgttgtcgg tgaaatttgt attactggac aatcagtatt   15420
tcttggttat ttagacaaaa ataaaaatta taagctagaa aaaataacat tgaataatga   15480
ggactataca atataccgta ctggagattt agcttattat gatgaaaatt atgatataca   15540
cttctttagc aggagttcca atttttgtgaa gataagaggt tatagaataa atcctaatga   15600
agtaacttct gcaataataa atcttcgtga agttaataat gcagttacac tggtattaaa   15660
tggacaactc atagcttatt atattggaga tgtagatgcg attgaaataa gaaaaaaaat   15720
aaaaaacatt cttccaaatt atatggttcc aacaactatt cataagctag atgcatttcc   15780
tatgacaatt aatgggaaaa tagatagtaa aaagttgaaa gaaataaaca ctgaaaaatg   15840
tagtctaaat agttatgaaa caaccgatag tagggataca ggatttatga atattgttat   15900
gaaagtgttt caaaataaaa aactaagtaa aaatgataac ttttatgatg ttggtgggga   15960
ttctattttg agtattaaac ttgccagtga attacaggat aatggattta atatttcttc   16020
agtagaaata atgaagtcaa atgattttaa tgaattattt caaaaaaata tacaacataa   16080
ttcaaaattt aatcaagatc ctgttttttgg aaaaatcaat ttattcccaa tgcagaaatg   16140 gttttttttct caagaatttc ataatattca tcattggaat caatcaaatg aatttgaaat   16200
atttggtcaa ttcgatgaat tagattttca aacaatttat tattcaatta gggagaaaca   16260
cgatgcaatt aggagttatt ttcaaagaat taatatggaa tattgctggt tggttaaaga   16320
aaataattta gaggattcaa aaaaagaaat tcaatatgtt gatagcagtc atttttaatat   16380 taataacata aatgaattaa aaagaaacct tcacaaaaca ataaatattt ttgatggacc   16440
attatctgca ataaagatta tcaaaataaa tgaaacgcat tttaaggtgc tgtgggttat   16500
gcatcattta atatgtgata acattagctg gttaattta aaaagggatt tcatacgtgc   16560
aattaattgc ttgaacaata ataagaaaat aactttatat cccaaatctt cgagtataga   16620
agattgggga aaatatataa taaaacagcc tcggttttca aatgatataa attcaaataa   16680
aaattcatca aaacacaaat atgaaactaa aaaaataaat attgtagaag atgattataa   16740
aaaagttaaa gaatattatc aaaaacataa tttgtctgaa gaaaatttcc tattattact   16800
ttttgcaaag gtactgagtg aacaaatggg aagagaaaag attttgatta ataaagaatt   16860
aagtggcaga aattatttgc cagaaaaata ttctcttgat caaactgtcg gttggtttac   16920
aaaaacttgt cctgttgaag tagattgtac tgtaccttat aaaagctttg tatctacaaa   16980
tatctttaac attgaaaagc aaacaagttt ttttaatgaa tattttttt cacaacctgt   17040 tagtggaccg gaaatatcat ttaacttttt aggcgaatta tcaaaagagt tagatgtaaa   17100
tgccatgcaa tcattcaatg atataggtga gtatgatttt ccggacaaaa tagctttttaa   17160 tgtattaaag agagaaaatg aatattcagt gtttattatt tatcaaagtg acatgtttca   17220
atattttgaa aaaataagtg agaatttatc aagcttgata aatctttttaa ctaaaatgga   17280 gagacagaat gtattcggta tctctgaaga ttcttttgaaa gttttaagcg attttatttta   17340 aaagaatggg gtgttaatat gaaagctata gctgcatatc ctatgactga agtgcaaaaa   17400
ggaatagcgt atgaatgtta tttaaataaa gacagagaat tttatattag tcaaatgaca   17460
atagagcttt actatgaaaa tatagagatt tataaagctg cttgggaaaa aattattgac   17520 aaaatatgaaa ccttcaaaac ggcatttttat tttggagaaa tgaaagatga tgttcaggta   17580
```

```
gttaataatc atattgattt caaatgggaa gtgttaactg attacaatgg tagtatagaa   17640
agtattgaag aaaaagaaag aaaaagatta tcagatataa agaaacccac acttattcgt   17700
tttaaacata ttaataataa tcagaaaaac tatttgatta ttactttcca tcatattatt   17760
ttagatggat ggagtttgtc tatagtcttg aatgatgtga atagacttta ttatcaatta   17820
tttaatgaag aaaaatcata tatttataat aatactgaat tcagtgaatt tattcaaaat   17880
aaattaactg ctaacaatga aaaatcgaat caatatttc aaaatttact tactgatttt   17940
cctggattta gtttcccttc tcttacacca atagaaaaag aaggttttga acaataaat   18000 aaaatactca ctctagatat gaaagtcatt aagaattttt gcaagaaata taaaatttcg   18060
ctatcttcac ttttagctc agtttggtct ttagttgtct cagcttatac aggtaaaagt   18120
gatattttac tgaataaaac gcattctgga cgggatagca aaaaaaaaga acaaattgtt   18180
gggttactta ttgaaaatta cccgtcacga tataaaattt acgatgatga gattcttaca   18240
gatttcattg aaaataatca tattactgat attgaaacaa gagaaaagca agaattttca   18300
atgtaccaaa caaaaaaata tttatcagat attggggtta atgaatacac aaattgtgct   18360
tttgtatatg aaaactatcc cgtaaatgaa agtaaatctt ataaaatatt aaacacattt   18420
gaaaagcagt caagcgaatt aactttatct gctggagtaa tgaatgatca agttttagta   18480
aaaatgatgt tttcattaga attaataaac aaagatatag catcggcctt aatagaatcc   18540
tatacagttt tgttaagcga agtttaaaa gatgagaaac aaactatcag tgaagtgatt   18600
aataaaatta gattaagtaa ggctttcgga gaggtacttc ctgtccctaa agatattcca   18660
ttaataactc atattgagga gagagtgcaa gggaaaaatg ataacattgc attttactat   18720
aacgataatg aaataaacta taatactta attaatgaga caaaaagata ttcatcctta   18780
ttaaacgatt tagagctttc ctatggagaa acagttgcta ttgattgtga tagagctccg   18840
tatgcaatat gtttaatgct tgcattagaa cagcatggca ttccatttgt atatttagat   18900
tccaaaaata ctagtgagag aaatcgattt atacttaatg attcaaatgc atcttatctt   18960
ttctatgata aaaaaaagcc ggaatatata agtgatatta aaattcgggg aataagtatt   19020
agcagtaaaa attcattcaa ctttaaaggg tctaacgagt atttgacaaa aacaaaaga   19080 gaagattatt ttcaaataat atatacatct ggtactacgg gcaacccaaa aggaataaaa   19140
ataactacga acaatatctt tgccttgtca atcaataatg gattttacga tgttaaagaa   19200
ggagatattt ttactcaagc ttcttcatta gcatttgatg catgcttttt tgaaatttgg   19260 ttacccctt taaataatgg gtcaattgct tttattccgg atccagtttt tgatgtacta   19320
agctggaaag aagtgctgaa taaatataat attacggcct cttggtttac ttcgagctta   19380
tttaatgtat ttattgatct agatccgtat ttattttcaa aaataagtaa tgtatttgtt   19440
ggtggtgaag cactctcaag agggcatgtt ttgaaagccc tttcagttaa ccctaatact   19500 aatttttta atggctatgg accgacagaa aatacaacat ttactacgac atataagata   19560
ccaacagatt atagtgaaag atcagcaatt tcaattggaa gcttattagc taattcagaa   19620
gcggttgttg ttgatgattc taatcgaatt gtaccgatat attctcaagg agagctattg   19680
gttcgtggga aagggttatc aaaaggttat gtggaaaaca aagttaatga taataaaaac   19740
ttcttagtag aaattaatga gcaaacttat tacagaacag gtgacattgt aagctttgat   19800
ggccagcgat tccattatat tgatagaaaa gatagccaag taaaaattaa tgggtatagg   19860
gtagaagtat tagagattga aaatagaatc aaagagataa ttggagtcaa aaatgcaaaa   19920
gttatgattg gagaagataa actgattact ctttttttata caggtggtat ttcaaaaaga   19980
```

```
gaattaaaga gtactttagc taacaagttc cctagttata tgaatcctaa acttgtatat   20040
cagataaaga ccatgcctct aactcttaac ggaaaaattg ataaagataa acttttaact   20100
ataaagaatg ataatggcca agaaaattta tctgaaataa agttgtggc tccaaaattg    20160 agtgatatta ttttaaaata tacagattct aaaaatatag aaagtgatgc tagctttcat   20220
gatttgggta ttgattccat gaaaacaatc agattgaata agaattaaa caaaatttt    20280 aatttggaag tatcattaaa agagtttgtt cagtttaaaa caattaatga tgttcaagag   20340
tattatatgt acgatattga aaatgaattc aagcaatcaa acggcaaata tttaggtttt   20400
gcaacaaaca tgcaaaagtc catgtactat taccaattag agcatccgga aaatacaatg   20460
tttaatattc cttatgttag aaaaattctt aaaacagata tgaaagtttc agatttaaat   20520
aataaagtaa aacaagtaat aggtgatcac aatatattta actcagcact tattgaagat   20580
aaaaatagcg atttaatatg ggtaactcaa aagaaaaatt ttgagataga acatattttt   20640
gtgccgggac aattcgataa gaataaaatt ataacttatt taaatcattc attcaattta   20700
agtgatggct tagaacctt aataaagta acttaattg aagaaaaag ctatatttat     20760 ttaattttg tagttcacca tattatattt gatggtatct ctctggagaa atttatctct    20820
atgatattcg acgatgaaca tttagacaat actaataact actttcaata tttgagtaca   20880
aaacaagatg aaaaaagta taaaaaggat aaagaatttt ggatggaaaa agtagttaat   20940
atagagaatt atttgcgctt ttataaaaag gaatttaatc atcaaggaga aatgcaatat   21000
tttgatattc cagaagaatt aggcgtactt atagaattgt tctcacaaaa aaataatata   21060
tcaaaattta atctttgctt gaagttatat agtcaattct tattaaacta ttttaatgaa   21120
gatgctgtat atgttggaac tccattaaat aagaggacgg aagaatataa aaatacgatt   21180
ggtttattta tagaattttt gcctgtcttg gataaaaaaa gtaacatcaa tacatttaaa   21240
gaagatgtac aaaactttaa attagaacta ttcgatttat atgatcatag tgatatagaa   21300
tttcaggata taaataacat acaagcaaca agaaataatt acgaacctat aacacaaaca   21360
acttttgcta tgcaaacttt ttctgaaaaa catagcaatg aattctatga tgatctaatt   21420
ataaaaaatc acaaatactc acagtttcca ttatcattaa ctatttatga atttacaaat   21480
tgtttgaagt tacaagttga ttatgctact gaattgttta ctagccaaga aattaaatct   21540
cttatagatt tattcttaat atggtcaaaa gaggtattac ttaaatcaga catttgtgta   21600
tcagatataa ttattagaga aactaaaaaa gaaataatac cattacctac tgaaaatcaa   21660
gaagaattta ggtttgaaca aataatatat ttagtaaatg aaaataatta cgatatacag   21720
atattagatg aaaattcaaa tgaaatacct gaaaatgaaa tagctaatgt atttttaata   21780
aaattaaaag tagaaagttc taatcaaaaa atgactgaaa atattaataa agttcataaa   21840
tgtcgttttt cagactcaag agatttaaat aaatcaatgt taaatacaag gctaaaggga   21900
tttaaaagtg gagaatcaat atttataaaa gataatgacg atcaaacatt taagatata    21960 attccgtttt taaattgtaa tatgaagaaa aataatgtaa atgaaagtag ttttaaatta   22020
aatgagctaa ttctgagtga tgttaaagaa gcatttaaaa aggtatttaa gattaaaaat   22080 ataataatg atgattcatt tcttaaatta ggtgggatt caatcaagaa tatccagatt     22140
atctcagcct taaggaagaa aaattacgtt ttatctacaa atgatttatt aaataatcca   22200
agtgtttccc tcttaacgaa gcatttacag aaaaacataa aaaataataa tatggcggtt   22260
aattataaat atctacaaaa attcaaattg aatataatgc agcaatggtt catgaaaaaa   22320
```

```
gataaaaaga attttcatca ttttaaccaa tcattttttg aaaacatcaa tattgatgta    22380
actaaagatg aattattaaa agcttttaaa tctctgtatt catcacatgc aatgttgcgt    22440
gctgtaattc tagaagagag aggagaatta tttaattata ttcaggaaat tgaaaattta    22500
aaatatgagc aaatatttat tgaatgtaag aacgaaaagg aattctataa taaagctaaa    22560
caagctgact tttcactgga tatatacaat ggaccaacat caaaaatatt atattttttt    22620
aataatcaaa agaattgtgt aggtgtttat tttgtttgtc atcatatgtt tgttgataca    22680
ttttcaataa atataattag aaatgaaatt aatgattttt tattgtatac aaagagagca    22740
acaggagata tttctaatac tgaactttg aataaaaaaa tacaaaacct acctagtatt    22800
aataccataa caaatcagaa gaatttaatt tattcttcaa aatcaggagt aatttcaagg    22860
aatatttcga tagaaaatag caaatattca caagtgaatt ttcctaaaat acttgcaagc    22920
agtattatta aagaaatttt gactgatgag tctttgaaac ttgacattgc tgttgaaaag    22980
gattcaagac tttcagaatc tttaaaagat tttaatctat ccgatactgt tgggtggtac    23040
actgaaatat ataatttaga tatacaacca gctatttcag tggaagaagt atacttaata    23100
ttgcaaaaag aaagtgatta taaatttcat cataagatta atagccaagt attttttaaat    23160 gttgtaaatc ttgaagaagc ccatgaatat aatgaatttt ttatatttga agaaattcaa    23220
tcaattgctg aagaaaatat acaatcaatg ccgccaacaa taaatattat taagcagggc    23280
tcgaacttga tggtaagcgt aatgaatatc aaaaactgtg aagaacatct tttaaatgcg    23340
attcatgaat ttaattgtta tattcaaaat gtaaattatt taaggtattt tgctgattta    23400
aaagtaattg gtaacccaat tatcccttt aaagagtatg ctgaactaat taatcaaaaa    23460
gaaattgaag aaatatatcc tttgtttcca ttacaagaag aaatgctgta ttcatctgtt    23520
ggagattatt cacaaagtta tattaatgaa atttcttgga ccactaaaac taatatgtct    23580
gatattatag agtcttttc caaagttcac cgaaaatatc aagctttgag aactaagttt    23640 tggattttcag ataatggctc agtgtatcag gtaattaaaa gttcttttga tgagttaccg    23700
attaaaatta tagatttaaa atatgtagat tcgaatgaga taattgagaa gatgaatgaa    23760
attaaagaaa gaatcattgg aaaattaaga gactttaaaa atggtgtaac tcattatctt    23820
ttaatcataa ctactccaaa taataataaa agaattgttt ggttattcaa tcatatttta    23880
ttcgatggtt ggagtttatc gattcttatt aatgaaatgt ggaataaaaa gactatactt    23940
ggaatcaatg aagtttcaaa cagggactat gtactttggc taaatcaaaa taaagaaacc    24000
atttctgagt caactgattt tcaatcacta ttaagtgaat tcaatggagt ttgtagcaat    24060
ctgtttaata acagggattt attacaaagt tctagagaag taaataggga agttagaatt    24120
actttagaaa aagagctaac taatgaaatt tacaaatatg ccaaacataa tgatataaaa    24180
gttgctcaaa tatttaacta tctatgggga tatattatta gccatctatc taaaaaatct    24240
aaagtaactt ttggtctagt cgactctggc cgtgaaataa atgtaccaga tatagaaaat    24300
aaagttggac tatttattaa gacattgcca atacttttta gcagagatga agataaaaca    24360
ataatcaatg agattaaaaa actagaagag gttaaatcta atattttttgc aaatgtaata    24420 agcataagta aattaaaaca aaacttaac attccaagtt ggcaattact ttatgatacg    24480
cttcttgtaa ttgaaaattt tccagaagtt gaagaacaac cagacagtat tcaagacttt    24540
tatgctagtg aacaatcgaa tatgccatta agtatgagtg tagggttatc aagtgatatt    24600 gttttttaaat tagtatattc cagttcactt atttcagaag aagctataga aaaaataagt    24660
agtatattta aagatttgct aaaacaagta tgctctctaa aatatgtact tagagtcaat    24720
```

```
gatttgttag tacctgatat tgagattaaa ctttcaaatg aaaatgttga cgaaatcaat   24780
tcagtaaaaa aagatacaaa taaaaataac aagatttgtg aagaagaaat tatcaatctg   24840
tgggaagaaa ttttaggtac acacagcgtt tcaactaatg atgatttctt tgaaagtggt   24900
ggcgattcgt taaagctttc taaattagta ttttattaa atgagaaaat gggattaaaa    24960
atggatgtta ttagcttctt tcaagaccca acaattcaaa acattttaaa caatgcaaac   25020
agtttaggca agcagtcaaa aaaagtaatg aagggtgatg atatagagtt acctaaattg   25080
ccctctactg aaatcttaaa agtagaaaat agtaataatc atgttttat tacaggaaca    25140 acgggattgc tagggagcga attgttatat caacaccta taaaaggatt tagtgtttat    25200
acagttatta gagcagaatg ttcaaaatca gcaagaaata gagtgttaaa acagctcaaa   25260
aaaatatcag gaaaaataga gaagctaccc ttagaaaatt tacatgtggt tgttggggat   25320
atttcaaaag aattttttcgg aatgtcacaa gaagaatatg ataaattatc aaaaacttgt  25380
tcagttattt ataattgtgc tagcaacgtg aattttatgg ctccctataa ggaagcatat   25440
aagtccaatg ttattggcgt tgaaaatata atgaaatttg ccaataataa attagttaag   25500
aaggtcaacc atatatcgac attgtctgta gttggacatg attattattt aattgaaaat   25560
ttggatgagg cgccaataag ttatattaaa acgaaaatac aagcagaaaa attattgaga   25620
aaataccgta caataaggaa tggtgtacaa atttcaagag taggtcgttt aaatggtaac   25680
tctcgtaata aaatgagccc aagtaaagat ttgttttgga gattgattttt atccattgct  25740 cagattggat gttgtcctca agaattttta gaacagcaaa cagatttaac acctgtggat   25800
gaggtagcta aatgcttaat gaattcgaat gcttctcata atgaaaatca aattataaat   25860
tattttacga aatcaatgat ttcatttggt gaatgtattc gtattattga agagattatc   25920
gataaaaaaa ttagaaaagt ttcattagaa gattggatat ttgaagcaga aaattcgaag   25980
gataatcata taaaaatatt aatcccacta tttaaagaaa atatcttta tgattctgga   26040 gtaaaggcaa ttaaaaattc aagttctgaa gatataggtt atcaaattaa ctacaatata   26100
aattgcagta taagttatga ttcactttat aaatatatct ataatgcctt agaaagtgag   26160
aggttattat gacaaatatt caagttctag catttcctta tgcgtgtggc tcactagata   26220
gttattcaaa attatgccat attgatggaa tagatttaat aaagtatgaa ttaccaggta   26280
gacgttctag aatatctgag aaattggatt cattaaattc agtcatgata gaggtttgta   26340
atgtgattaa ttttaattct ccatatgtca ttttttggtca tagtatgggg ggatatttag  26400
caaatgaatt atgtaggttt attgagatta ataagctcca taaacctcgg aaagtcatta   26460
ttagtgggca atgccctgtt gacaacaata tgatagcct agaagaatat aatgaactat    26520
ctttggataa tacgaaaact tatatatcat tgtttaatgg aactcctcaa gaaataatta   26580
ataataaaga actaatggaa ttctatggtg aaatatttta tcaggatatg cagtttatca   26640
atcaatataa aatgaataat agttctaaaa aggtaaagtc taatgttgaa gtttggtata   26700
gtgatcaaga tattcatgta aaagaagaaa atattatgaa atggaaggat tacgctgtaa   26760
attcatgcaa ttttaaaaag tttaaaggag atcacttttt tatcaataat atatttcaag   26820
atccgaagtt aactttcgaa ctcttgtgtt gctaatttat atcttaagct tagctagaag   26880
gagagaattt atatgtctaa attgcattta aatgaattat ataaaaaata taacaatact   26940
caaaagctga tagaatcaag taaaagctt catgagttct tattggacaa tgtgaagaaa    27000
catccagata agattgcagt tagaaacaaa aaagaaagta ttacttatga acagctatac   27060
```

-continued

| | | | | | |
|---|---|---|---|---|---|
| aataaaatga | ttgaggtaac | taacttattt | gattttaata | atcagccaat | tgcaataatg | 27120 |
| ggatataaaa | atatagatgt | agttggacaa | attttaggag | tcttgaattc | aggcaatttc | 27180 |
| tttataccaa | ttaatccagc | ttcgccagat | gaaaggataa | attatatttt | agataaaaca | 27240 |
| caagcgaaag | cgttcattga | ctgcaagaac | acctattttt | tacatgataa | agtaaatgtc | 27300 |
| gtcaatacta | ttaaaccatt | agttggggat | gattcccttg | cttatgtgat | ttttacttcg | 27360 |
| ggaactactg | gaatgccaaa | aggagtcata | gaatctcatt | atcaagttgt | gaacaccatc | 27420 |
| ttcgatttaa | ttgaaagatt | tgatttagat | gatactgatt | attttttaaa | tctatcatcc | 27480 |
| ctatcatttg | atttaagcat | ttttgatata | tttgcctcaa | taattgttgg | agggacattg | 27540 |
| catttagttg | aagatcctag | agattttaat | gaaattaata | tgattctttc | aaaatatcca | 27600 |
| gtaacgattt | ggaattccgt | acctaactta | atgtatcttt | atttaaactc | caataaagtt | 27660 |
| atagagaata | aattaaaaca | ttgtttacta | agtggagatt | ttatttcagt | aggattagct | 27720 |
| aaactttttt | ataagaatt | acccaatgtg | aatttgcata | gtttaggagg | agcaactgag | 27780 |
| ggtactattt | ggtcaattac | ttataatgtt | atgaaaaatg | aggtaaatca | attgaaatat | 27840 |
| attccctacg | ggtatccttt | aaccaaccaa | acgatatata | tattaaataa | tgaacatgat | 27900 |
| ttttgtgatg | taggggaagt | tggagaaatt | gctattggtg | gaatgggagt | agcccatggg | 27960 |
| tatataaatg | accagtttaa | aactagtaaa | tcgtttatac | atcatcctag | attgggatat | 28020 |
| atttatctaa | ctggtgactt | aggtatctat | acggaacata | attatattaa | aatacttggt | 28080 |
| aggaagaatg | atgattttaa | agttaatggt | tatcgattga | gtttaagcga | aatttccaat | 28140 |
| aagtttaata | agtgtttcaa | tactgaaagc | cgtattcttt | taacaaaaga | tactcctaaa | 28200 |
| aagatgatta | ttgcatatga | aggcgaaatt | tcgtcagata | aaaatgaaat | attaaaaaaa | 28260 |
| ttatctaact | atttattacc | ttacgaaatg | cccaattatg | tatttaaggt | agaaagattt | 28320 |
| cctatcacaa | ttaatggaaa | aactgattat | aataagttat | ttgatatcta | catggagcag | 28380 |
| cgtcacttta | tacgtaagaa | taaagatagt | accgatgatg | tgagtactga | gctaagaaag | 28440 |
| atgttatctt | tggaacttga | tgtgacaaat | attcaatcta | cagatacttt | gttagatttt | 28500 |
| ggagttgatt | ccattcaaat | gatgaggatt | aagatttgga | ttgaaaataa | aattgggcga | 28560 |
| gaattagaaa | tgattgaact | gtatgaaaat | aactcagtga | aagagttaga | aactctatta | 28620 |
| actgaaaggt | gaaactataa | tgctgatgat | ttatatttat | gaaaataaga | aaagtgtatt | 28680 |
| ttctacaata | gagaccaagt | tacttaattt | tatacaggaa | gaagatttga | acaaaatcgc | 28740 |
| cgctttatat | tacgatagag | ataaactaaa | tttgctatat | agtagattag | tggttttgta | 28800 |
| tggaatgtat | aagcttagag | gtatttctcc | taatgatgta | aatatattaa | agaaaaata | 28860 |
| cggtaaaccg | tatattgaga | ataataacat | ttacttttat | atatcacatt | ctggtaaagt | 28920 |
| tgtttatgtt | gcatttttatg | aacatggtga | agtaggaatt | gacgttgaag | aattaaatga | 28980 |
| cgttcctaat | gaaattattg | aatattgctt | tcatgaagaa | gaaaaaaat | taatgaaaag | 29040 |
| agctaaaaaa | cgtgaatata | agaggcgatt | ttatgatatt | tggacaaaaa | aagaagcata | 29100 |
| tttaaagaaa | aaaggtactg | gtatttcaga | taatttaaaa | aagtaaatg | taactaaaaa | 29160 |
| atatgatttt | attacttttg | aatggaataa | ttactattgt | tcggttactg | ctgacggttt | 29220 |
| aaaaacatat | agtattaaaa | tcattcagtt | tgaggaacta | attcattttt | taagtcatt | 29280 |
| ttctagtttt | taaatagaat | ttgaactaag | aggctgtttt | ttaaatagga | caattcattt | 29340 |
| aagttatgga | agttaagtga | cggatgctta | acttcttttt | aaattaagat | gtgaatagtc | 29400 |
| ttgaacctat | gagcattcta | aaacacaaat | tatcatatat | tccatagtca | aaagataatc | 29460 |

```
tttttattat ctgaatttta tgtttaatta tctctataga ccgttgtaaa gtcttgaata  29520
attgattata tttcaattaa ggttattatc tgttttaatg ttctaattat tggaaggatc  29580
tttgtacaaa atagctgata aatta                                        29605
```